(12) United States Patent
Morad et al.

(10) Patent No.: US 11,739,163 B2
(45) Date of Patent: Aug. 29, 2023

(54) THERAPEUTIC MULTI-TARGETING CONSTRUCTS AND USES THEREOF

(71) Applicant: AEBI LTD., Ness Ziona (IL)

(72) Inventors: Ilan Morad, Ness Ziona (IL); Hanan Itzhaki, Ness Ziona (IL)

(73) Assignee: AEBI LTD., Ness Ziona (IL)

( * ) Notice: Subject to any disclaimer, the term of this patent is extended or adjusted under 35 U.S.C. 154(b) by 271 days.

(21) Appl. No.: 16/337,163

(22) PCT Filed: Sep. 27, 2017

(86) PCT No.: PCT/IL2017/051094
§ 371 (c)(1),
(2) Date: Mar. 27, 2019

(87) PCT Pub. No.: WO2018/061004
PCT Pub. Date: Apr. 5, 2018

(65) Prior Publication Data
US 2019/0225711 A1 Jul. 25, 2019

Related U.S. Application Data

(60) Provisional application No. 62/401,192, filed on Sep. 29, 2016, provisional application No. 62/401,195, filed on Sep. 29, 2016.

(51) Int. Cl.

| C07K 17/08 | (2006.01) |
|---|---|
| A61K 47/60 | (2017.01) |
| A61P 35/00 | (2006.01) |
| C07K 7/08 | (2006.01) |
| C07K 14/82 | (2006.01) |
| C07K 14/47 | (2006.01) |
| A61K 47/62 | (2017.01) |
| A61K 47/64 | (2017.01) |
| C07K 14/33 | (2006.01) |
| C07K 14/705 | (2006.01) |
| A61K 38/00 | (2006.01) |

(52) U.S. Cl.
CPC .............. C07K 17/08 (2013.01); A61K 47/60 (2017.08); A61K 47/62 (2017.08); A61K 47/6415 (2017.08); A61P 35/00 (2018.01); C07K 7/08 (2013.01); C07K 14/33 (2013.01); C07K 14/4748 (2013.01); C07K 14/70532 (2013.01); C07K 14/82 (2013.01); A61K 38/00 (2013.01); C07K 2319/00 (2013.01); C07K 2319/33 (2013.01); C07K 2319/40 (2013.01); C07K 2319/55 (2013.01)

(58) Field of Classification Search
CPC .. C07K 17/08; C07K 14/33; C07K 14/70532; A61K 47/6415; A61K 47/60; A61P 35/00
See application file for complete search history.

(56) References Cited

U.S. PATENT DOCUMENTS

| 7,947,289 B2 | 5/2011 | Leppla | |
|---|---|---|---|
| 9,220,791 B2 | 12/2015 | Stayton | |
| 9,234,021 B2 | 1/2016 | Cochran | |
| 2004/0058865 A1 | 3/2004 | Danishefsky | |
| 2009/0130105 A1 | 5/2009 | Glaser | |
| 2010/0151003 A1 | 6/2010 | Trikha | |
| 2014/0065142 A1* | 3/2014 | Roschke | .............. C07K 16/241 424/134.1 |
| 2015/0065711 A1 | 3/2015 | Davis | |
| 2020/0339629 A1 | 10/2020 | Morad | |

FOREIGN PATENT DOCUMENTS

| EP | 2865686 A1 | 4/2015 |
|---|---|---|
| JP | 2007524598 A | 8/2007 |
| JP | 2009518025 A | 5/2009 |
| JP | 2010154842 A | 7/2010 |
| JP | 2011517314 A | 6/2011 |
| JP | 2015509501 A | 3/2015 |
| JP | 2016512508 A | 4/2016 |
| JP | 2016526892 A | 9/2016 |
| WO | 2007010525 A2 | 1/2007 |
| WO | 2007066109 A1 | 6/2007 |
| WO | 2007093373 A2 | 8/2007 |
| WO | 2008088422 A2 | 7/2008 |
| WO | 2010064207 A2 | 6/2010 |
| WO | 2011047135 A2 | 4/2011 |
| WO | 2011115712 A2 | 9/2011 |
| WO | 2013126690 A1 | 8/2013 |
| WO | 2013164694 A1 | 11/2013 |
| WO | 2015010094 A1 | 1/2015 |
| WO | 2015195721 A1 | 12/2015 |
| WO | 2019064297 A1 | 4/2019 |

OTHER PUBLICATIONS

Jones, Pharmacogenomics Journal (2001) 1:126-134. (Year: 2001).*
Tosatto et al., Current Pharmaceutical Design (2006), 12:2067-2086. (Year: 2006).*
Li et al., (2017) Identification and characterization of a novel peptide ligand of epidermal growth factor receptor for targeted delivery of therapeutics. FASEB J 19(14): 1978-1985.
Morad and Itzhaki (2020) MuTaTo ©—A Novel Concept for Curing Cancer. Journal of Cancer Therapy 11: 55-73.
Narang and Desai (2009) Anticancer Drug Development. Unique Aspects of Pharmaceutical Development. In: Lu Y and Mahato R (eds) Pharmaceutical Perspectives of Cancer Therapeutics. Springer, New York, USA; pp. 49-92.

(Continued)

Primary Examiner — Meera Natarajan
Assistant Examiner — Cheom-Gil Cheong
(74) Attorney, Agent, or Firm — Raphael Bellum PLLC

(57) ABSTRACT

The present invention provides constructs comprising a plurality of peptides capable of targeting at least two different extracellular tumor antigens and a toxin, optionally connected to an organic scaffold. Use of such constructs in treating cancer are provided as well. The invention also provides particular peptides binding certain extracellular tumor antigens as well as toxins having antitumor activity.

4 Claims, 14 Drawing Sheets

Specification includes a Sequence Listing.

(56) References Cited

OTHER PUBLICATIONS

Pang (2000) Targeting and eradicating cancer cells by a prostate-specific vector carrying the diphtheria toxin A gene. Cancer Gene Ther 7(7): 991-996.
Sierra and Tsao (2011) c-MET as a potential therapeutic target and biomarker in cancer. Ther Adv Med Oncol 3(1 Suppl): S21-S35.
Zhang et al., (2016) Tumor-penetration and antitumor efficacy of cetuximab are enhanced by co-administered iRGD in a murine model of human NSCLC. Oncol Lett 12(5): 3241-3249.
Billen et al., (2008) Two novel sodium channel inhibitors from Heriaeus melloteei spider venom differentially interacting with mammalian channel's isoforms. Toxicon 52(2): 309-317.
Bláha et al., (2009) Toxins produced in cyanobacterial water blooms—toxicity and risks. Interdiscip Toxicol 2(2): 36-41.
Chang et al., (2015) Blocking of the PD-1/PD-L1 Interaction by a D-Peptide Antagonist for Cancer Immunotherapy. Angew Chem Int Ed Engl 54(40): 11760-11764.
DeNardo et al., (2003) Effect of molecular size of pegylated peptide on the pharmacokinetics and tumor targeting in lymphoma-bearing mice. Clin Cancer Res 9(10 Pt 2): 3854S-3864S.
Dings et al., (2010) Inhibiting tumor growth by targeting tumor vasculature with galectin-1 antagonist anginex conjugated to the cytotoxic acylfulvene, 6-hydroxylpropylacylfulvene. Bioconjug Chem 21(1): 20-27.
Douillard et al., (2000) Irinotecan combined with fluorouracil compared with fluorouracil alone as first-line treatment for metastatic colorectal cancer: a multicentre randomised trial. Lancet 355(9209): 1041-1047.
Dyba et al., (2004) Small molecule toxins targeting tumor receptors. Curr Pharm Des 10(19): 2311-2334.
Fields and Noble (1990) Solid phase peptide synthesis utilizing 9-fluorenylmethoxycarbonyl amino acids. Int J Pept Protein Res 35(3): 161-214.
Gautam et al., (2014) Tumor homing peptides as molecular probes for cancer therapeutics, diagnostics and theranostics. Curr Med Chem 21(21): 2367-2391.
Gilly et al., (2011) A diverse family of novel peptide toxins from an unusual cone snail, *Conus californicus*. The Journal of Experimental Biology 214: 147-161.
Hunt, H (2013) Tumor homing peptides for drug delivery and imaging. Utrecht University, The Netherlands. Graduate School of Life Sciences, Master program Drug Innovation. 24 pages.
Kisiel et al., (2004) Structural determinants of the selectivity of KTS-disintegrins for the alphalbetal integrin. FEBS Lett 577(3): 478-482.
Kohno et al., (2011) A novel hybrid peptide targeting EGFR-expressing cancers. Eur J Cancer 47(5): 773-783.
Li et al., (2005) Identification and characterization of a novel peptide ligand of epidermal growth factor receptor for targeted delivery of therapeutics. FASEB J 19(14): 1978-1985.
McGuire et al., (2014) Identification and characterization of a suite of tumor targeting peptides for non-small cell lung cancer. Sci Rep 4: 4480; 11 pages.
Mishra et al., (2016) PEGylation in anti-cancer therapy: An overview. Asian Journal of Pharmaceutical Sciences 11(3): 337-348.
Muchiri Ruth Njeri (2010) "Arg-Gly-Asp (RGD) Tumor Targeting Conjugates". Michigan State University, Department of Chemistry. 61 pages.
Nicolaou et al., (1994) Calicheamicin θ : A Rationally Designed Molecule with Extremely Potent and Selective DNA Cleaving Properties and Apoptosis Inducing Activity. Agnew Chem Intl Ed Engl 33(2): 183-186.
Saltz et al., (1999) Weekly irinotecan (CPT-11), leucovorin (LV), and fluorouracil (FU) is superior to daily $\times$ 5 LV/FU in patients (PTS) with previously untreated metastatic colorectal cancer (CRC). Abstract No. 898. Proc Am Soc Clin Oncol 18: 233a.
Smith et al., (2007) Molecular interactions of the gating modifier toxin ProTx-II with NaV 1.5: implied existence of a novel toxin binding site coupled to activation. J Biol Chem 282(17): 12687-12697.
Tsai et al., (2011) A novel bispecific ligand-directed toxin designed to simultaneously target EGFR on human glioblastoma cells and uPAR on tumor neovasculature. J Neurooncol 103(2): 255-266.
Weigel et al., (2015) Design and evaluation of a peptide-based immunotoxin for breast cancer therapeutics. FEBS Open Bio 5: 202-208.
Wu et al., (2014) Peptide-based cancer therapy: opportunity and challenge. Cancer Lett 351(1): 13-22.
Arrowhead Research Corporation; Homing Peptides. Retrieved from: http://www.arrowheadresearch.com/technology/homingpeptides on Sep. 10, 2015 (Sep. 10, 2015). 2 pages.
IARC Working Group on the Evaluation of Carcinogenic Risks to Humans (2010) Cyanobacterial Peptide Toxins. In: IARC Monographs on the Evaluation of Carcinogenic Risks to Humans. Ingested Nitrate and Nitrite, and Cyanobacterial Peptide Toxins. World Health Organization, International Agency for Research on Cancer. Lyon, France. vol. 94, pp. 329-412.
Immunwork, Inc.; Overview. Retrieved from: http://www.immunwork.com/edcontent_d.php?lang=en&tb=1&id=59 on Aug. 5, 2019. 1 page.
Peptide Toxins; Synthetic Ion Channel Blockers for Pain Research. Peptides International, Inc., pepnet.com; Louisville, KY, USA. Retrieved on Dec. 2, 2014, 4 pages.
Kawakami (2009) Forefront of anti-cancer molecular targeted immunotoxin therapy. Farumashia 45(9): 923-924. With machine translation.

* cited by examiner preincubation in serum (min)

THERAPEUTIC MULTI-TARGETING CONSTRUCTS AND USES THEREOF

FIELD OF THE INVENTION

The invention relates to constructs comprising a plurality of peptides capable of targeting at least two different extracellular tumor antigens and at least one toxin, optionally connected to an organic scaffold and use of such constructs in treating cancer are provided as well. The invention also relates to particular peptides binding certain extracellular tumor antigens as well as toxins having antitumor activity, and conjugates of these peptides and toxins.

BACKGROUND OF THE INVENTION

Targeted cancer therapies are drugs or other substances designed to interfere with specific molecules involved in cancer cell growth and survival. In contrast to traditional chemotherapy drugs, which usually act against all actively dividing cells, a primary goal of targeted therapies is to fight cancer cells with more precision and potentially fewer side effects. Targeted cancer therapies that have been approved for use against specific cancers include agents that prevent cell growth signaling, interfere with tumor blood vessel development, promote the death of cancer cells, stimulate the immune system to destroy cancer cells, and deliver toxic drugs to cancer cells. The latter mainly includes monoclonal antibodies that deliver toxic molecules. Once the antibody has bound to its target cell, the toxic molecule that is linked to the antibody, such as a radioactive substance, a toxic polypeptide or a poisonous chemical, is taken up by the cell, ultimately killing that cell. The toxin will not affect cells that lack the target for the antibody.

Efficient tumor targeting is challenging for a number of reasons. First, it requires identifying a target that is sufficiently specific to the tumor cells to avoid as much as possible non-specific killing of cells. In addition, cancer cells tend to be variable, both between cancer types and within the same type of cancer: the expression pattern of surface targets may vary between cells of a particular tumor. Cancer cells may also alter expression of their cell surface receptors during tumor development or become resistant to the therapy. Resistance may occur in two ways: the target itself changes through mutation so that the targeted therapy no longer interacts well with it, and/or the tumor finds a new pathway to achieve tumor growth that does not depend on the target. Most anti-cancer drugs attack a specific target on, or in, the cancer cell. Inhibiting the target usually aims to block a physiological pathway that promotes cancer. Mutations in the targets, or in their downstream physiological pathways, make the targets not relevant to the cancerous nature of the cell.

DeNardo et al., 2003, *Clin Cancer Res.* 9(10 Pt 2): 3854S-64S report about the synthesis of branched poly (ethylene glycol) (PEGylated) polymers (Mr 40,000, Mr 70,000, Mr 100,000, and Mr 150,000) conjugated to tumor-specific or control peptides, to assess the effect of both molecular weight and tumor specificity on pharmacokinetics and biodistribution.

Tsai et al., 2011, *J Neurooncol.* 103(2): 255-266, describe a bispecific ligand-directed toxin designed to simultaneously target epidermal growth factor receptor (EGFR) on human glioblastoma cells and urokinase receptor (uPAR) on tumor neovasculature. The construct is a single-chain polypeptide consisting of human epidermal growth factor (EGF), a fragment of urokinase and truncated *pseudomonas* exotoxin (PE38).

McGuire et al., 2014, *Sci Rep.*, 4:4480 report about the characterization of a suite of tumor targeting peptides for non-small cell lung cancer identified from phage-display libraries. The peptides were synthesized as monomers and homo-tetramers.

U.S. Pat. No. 7,947,289 discloses compositions comprising modified bacterial toxins and methods for using the modified bacterial toxins for targeting particular cell populations and for treating diseases.

US 2004/0058865 discloses synthetic multimeric ligands that provide for enhanced cell-, and organ-specific targeting, and methods of their preparation and use.

US 2009/0130105 discloses compositions that bind to multiple epitopes of IGF-1R, for example, combinations of monospecific binding molecules or multispecific binding molecules (e.g., bispecific molecules). Methods of making the subject binding molecules and methods of using the binding molecules to antagonize IGF-1R signaling are also disclosed.

WO 2007/093373 discloses in vivo stable branched peptides, in particular derived from the sequence of Neurotensin (NT) and Luteinizing hormone-releasing hormone (LHRH), conjugated to functional units for specific targeting of cancer cells, either for tumor diagnosis or therapy.

WO 2008/088422 discloses a composition of matter comprising an OSK1 peptide analog, and in some embodiments, a pharmaceutically acceptable salt thereof. Further disclosed are pharmaceutical compositions comprising the composition and a pharmaceutically acceptable carrier, DNAs encoding the composition of matter, an expression vector comprising the DNA, and host cells comprising the expression vector. Methods of treating an autoimmune disorder and of preventing or mitigating a relapse of a symptom of multiple sclerosis are also disclosed.

There still remains an unmet need for improved compositions and methods for targeted cancer therapy, with enhanced potency and reduced adverse non-specific effects.

SUMMARY OF THE INVENTION

The present invention relates to a construct comprising at least two different peptides binding to at least two different extracellular tumor antigens, and at least one toxin, wherein the peptides and the toxin are covalently bound directly or through a carrier. The invention is based on an unexpected observation that a construct comprising two peptides binding two different targets on cancer cells and a toxin has an advantageous and, in some cases, a synergic cytotoxic effect in comparison to constructs having only one of these peptides.

According to one aspect, the present invention provides a construct comprising at least two different peptides binding to at least two different extracellular tumor antigens, and at least one toxin, wherein the peptides and the toxin are covalently bound directly or through a carrier.

According to some embodiments of the invention, at least one of the peptides binds specifically to an extracellular tumor antigen selected from human epidermal growth factor receptor (EGFR) and human Programmed death-ligand 1 (PD-L1). In certain embodiments, the another one of the at least two peptides binds specifically to an extracellular tumor antigen selected from the group consisting of EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR.

According to some embodiments, the construct can comprise from 3 to 10 different peptides binding to different extracellular tumor antigens.

In some embodiments, the present invention provides a construct comprising at least two different peptides binding to at least two different extracellular tumor antigens, and at least one toxin, wherein the peptides and the toxin are covalently bound directly or through a carrier and wherein at least one of the peptides binds specifically to EGFR. In one embodiment, peptide comprises the amino acid sequence as set forth in SEQ ID NO: 1 (CHPGDKQEDPN-CLQADK) or being an analog thereof.

In other embodiments, the present invention provides a construct comprising at least two different peptides binding to at least two different extracellular tumor antigens, and at least one toxin, wherein the peptides and the toxin are covalently bound directly or through a carrier and wherein at least one of the peptides binds specifically to PD-L1. In one embodiment, the peptide comprises the amino acid sequence as set forth in SEQ ID NO: 2 (CEGLPAD-WAAAC) or being an analog thereof.

In certain embodiment, the present invention provides a construct comprising at least two different peptides binding to at least two different extracellular tumor antigens, and at least one toxin, wherein the peptides and the toxin are covalently bound directly or through a carrier and wherein one of the peptides binds specifically to EGFR and one of the peptides binds specifically to PD-L1. According to one embodiments, the EGFR the peptide that binds specifically to EGFR is a peptide having SEQ ID NO: 1 or an analog thereof, and the peptide that binds specifically to PD-L1 is a peptide having SEQ ID NO: 2 or an analog thereof.

According to any one of the above embodiments, the construct comprises multiple copies of at least one or of at least two of the peptides. In some embodiments, the construct comprises from 2 to 50 copies of at least one of the peptides.

According to any one of the above embodiments, the toxin is a peptide, polypeptide or protein toxin. In some embodiments, the toxin is selected from a toxin binding to a eukaryotic elongation factor 2, BIM-BH3 consisting of SEQ ID NO: 5, Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, and cyanotoxin. In one embodiments, the toxin binding to eukaryotic elongation factor 2 is a toxin comprising the amino acid sequence selected from SEQ ID NO: 3 (CSARWGPTMPWC), SEQ ID NO: 4 (CRRGSRASGAHC), or an analog thereof. According to some embodiments, the construct comprises 2 to 10 different toxins. According to certain embodiments, the construct comprises a toxin having SEQ ID NO: 3 and a toxin having SEQ ID NO: 4.

According to any one of the above embodiments, the construct comprises multiple copies of at least one or of at least two of the toxins. According to one embodiment, the construct comprises from 2 to 50 copies of the at least one of the toxins. According to another embodiment, the construct comprises 2 to 50 copies of a toxin having SEQ ID NO: 3 and 2 to 50 copies of a toxin having SEQ ID NO: 4.

According to some embodiments, the present invention provides a construct, wherein one of the peptides binds specifically to EGFR and one of the peptides binds specifically to PD-L1 and the toxin is selected from a toxin binding specifically to eukaryotic elongation factor 2 and a toxin having SEQ ID NO: 5. According to one such embodiment, the construct comprises a peptide having SEQ ID NO: 1 or an analog thereof, a peptide having SEQ ID NO: 2 or an analog thereof, and at least one toxin having amino acid sequence selected from SEQ ID NO: 3, 4, and 5. According to one embodiment, the construct comprises a peptide comprising SEQ ID NO: 1 or an analog thereof, a peptide comprising SEQ ID NO: 2 or an analog thereof, a toxin comprising SEQ ID NO: 3, and a toxin comprising SEQ ID NO: 4. According to any one of such embodiments, the construct comprises multiple copies of each one of the peptides and the toxin(s).

According to any one of the above embodiments, at least one of the peptides and/or at least one toxin are covalently bound through a carrier. According to one embodiment, the carrier is an organic scaffold. According to another embodiment, each one of the peptides and of the toxin(s) are bound to a carrier, wherein the carrier is an organic scaffold. According to some embodiments, the scaffold is a polyethylene glycol (PEG) molecule or a modified PEG molecule. According to one embodiments, the PEG molecule is a branched molecule. According to another embodiment, the PEG molecules comprises a plurality of sites for binging the peptides and/or the toxin(s) of the present invention. According to one embodiment, the PEG molecule comprises 8 to 56 sites available to bind the peptides and the toxin(s).

According to some embodiments, the present invention provides a construct comprising multiple copies of each one of at least two different peptides binding to at least two different extracellular tumor antigens, and at least one toxin, wherein the peptides and the toxin(s) are bound to the scaffold and wherein at least one of the peptides binds specifically to the extracellular tumor antigens selected from EGFR or PD-L1. According to some embodiments, one of the peptides binds specifically to EGFR and one of the peptides binds specifically to PD-L1. According to one embodiment, the peptide that binds specifically to EGFR is a peptide having SEQ ID NO: 1 or an analog thereof, and the peptide that binds specifically to PD-L1 is a peptide having SEQ ID NO: 2 or an analog thereof. According to certain embodiments, the toxin comprises the amino acid sequence selected from SEQ ID NO: 3, 4 and 5, or an analog thereof. According to one embodiments, the scaffold is PEG scaffold. According to one embodiment, the PEG molecule comprises 8 to 56 sites available to bind the peptides and the toxin(s).

According to one embodiment, the construct comprises multiple copies of each one of the: (i) a peptide having SEQ ID NO: 1, (ii) a peptide having SEQ ID NO: 2, (iii) a toxin having SEQ ID NO: 3 and (iv) a toxin having SEQ ID NO: 4, wherein each one of the peptides and the toxins is bound to the scaffold. According to one embodiments, the scaffold is PEG scaffold. According to another embodiment, the construct comprises multiple copies of each one of the: (i) a peptide consisting of SEQ ID NO: 1, (ii) a peptide consisting of SEQ ID NO: 2, (iii) a toxin consisting of SEQ ID NO: 3, and (iv) a toxin consisting of SEQ ID NO: 4. According to some embodiments, the stoichiometric molar ratio between the peptide having or consisting of SEQ ID NO: 1, the peptide having or consisting of SEQ ID NO: 2, the toxin having or consisting of SEQ ID NO: 3 and the toxin having or consisting of SEQ ID NO: 4 is 1:1:3:3.

According to any one of the above embodiments, at least one of the peptides or of the toxins is connected to the scaffold through a linker or spacer.

According to any one of the above embodiments, the construct further comprises a permeability-enhancing moiety.

According to another aspect, the present invention provides a composition comprising a construct of the present invention. According to one embodiment, the composition is a pharmaceutical composition. Thus, in some embodiments, the present invention provides a pharmaceutical composition comprising a construct of the present invention and a pharmaceutically acceptable excipient. According to one embodiment, the pharmaceutical composition comprises a construct comprising multiple copies of each one of at least two different peptides binding to at least two different extracellular tumor antigens, and at least one toxin, wherein the peptides and the toxin(s) are bound to the scaffold and wherein at least one of the peptides binds specifically to the extracellular tumor antigens selected from EGFR or PD-L1. According to some embodiments, one of the peptides binds specifically to EGFR and one of the peptides binds specifically to PD-L1. According to one embodiment, the peptide that binds specifically to EGFR is a peptide having SEQ ID NO: 1 or an analog thereof, and the peptide that binds specifically to PD-L1 is a peptide having SEQ ID NO: 2 or an analog thereof. According to certain embodiments, the toxin comprises the amino acid sequence selected from SEQ ID NO: 3, 4 and 5, or an analog thereof. According to one embodiments, the scaffold is PEG scaffold.

According to one embodiment, the pharmaceutical composition comprises a the construct comprising multiple copies of each one of the: (i) a peptide having SEQ ID NO: 1, (ii) a peptide having SEQ ID NO: 2, (iii) a toxin having SEQ ID NO: 3 and (iv) a toxin having SEQ ID NO: 4, wherein each one of the peptides and the toxins is bound to the scaffold. According to one embodiments, the scaffold is PEG scaffold. According to another embodiment, the construct comprises multiple copies of each one of the: (i) a peptide consisting of SEQ ID NO: 1 (ii) a peptide consisting of SEQ ID NO: 2, (iii) a toxin consisting of SEQ ID NO: 3, and (iv) a toxin consisting of SEQ ID NO: 4. According to some embodiments, the stoichiometric molar ratio between the peptide having or consisting of SEQ ID NO: 1, the peptide having or consisting of SEQ ID NO: 2, the toxin having or consisting of SEQ ID NO: 3 and the toxin having or consisting of SEQ ID NO: 4 is 1:1:3:3.

According to one embodiment, the pharmaceutical composition of the present invention is for use in treating cancer.

According to certain aspects, the present invention provides a method of treating cancer in a subject in need thereof comprising administering to said subject a pharmaceutical composition of the present invention. According to one embodiment, the pharmaceutical composition comprises a construct of the present invention. According to one embodiment, the present invention provides a method of treating cancer in a subject in need thereof comprising administering a therapeutically effective amount of the construct of the present invention.

According to one aspect, the present invention provides a peptide that binds specifically to human eukaryotic Elongation Factor 2 (eEF2), wherein the peptide comprises the amino acid sequence selected from SEQ ID NO:3, SEQ ID NO: 4 and an analogs thereof. According to one embodiment, the peptide or the analog is cyclic. According to one embodiment, the peptide comprising or consisting of SEQ ID NO:3, or an analog thereof enhances eEF2 activity. According to another embodiment, the peptide comprising or consisting of SEQ ID NO:4, or an analog thereof enhances eEF2 activity. According to one embodiment, the peptide or analog is for use in inducing cell death.

According to another aspect, the present invention provides a peptide comprising the amino acids sequence set forth in SEQ ID NO: 1 or an analog thereof. According to one embodiment, the peptide or the analog is an antagonist of a human Epidermal Growth Factor Receptor (EGFR). According to another embodiment, the peptide or the analog is cyclic. According to one embodiment, the peptide or the analog is for use in targeting cancer cells.

According to a further embodiment, the present invention provides a peptide comprising the amino acids sequence set forth in SEQ ID NO: 2 or an analog thereof. According to one embodiment, the peptide or the analog is an antagonist of a human Programmed death-ligand 1 (PD-L1). According to another embodiment, the peptide or the analog is cyclic. According to one embodiment, the peptide or the analog is for use in targeting cancer cells.

According to certain aspects, the present invention provides a conjugate comprising at least one peptide of the present invention. According to one embodiment, the peptide is selected from a peptide comprising or consisting of SEQ ID NO:1, a peptide comprising or consisting of SEQ ID NO:2, a peptide comprising or consisting of SEQ ID NO:3, a peptide comprising or consisting of SEQ ID NO: 4 and an analog of said peptides.

According to another aspect, the present invention provides a composition comprising the peptide of the present invention or the conjugate of the present invention. According to one embodiment, the composition is a pharmaceutical composition. Thus, in some embodiments, the present invention provides a pharmaceutical composition comprising the peptide of the present invention or the conjugate of the present invention. According to one embodiment, the peptide is selected from a peptide comprising or consisting of SEQ ID NO:1, a peptide comprising or consisting of SEQ ID NO:2, a peptide comprising or consisting of SEQ ID NO:3, a peptide comprising or consisting of SEQ ID NO: 4 and an analog of said peptides. According to another embodiment, the conjugate is a conjugate of said peptides. According to some embodiments, the pharmaceutical composition is for use in treating cancer.

According to one aspect, the present invention provides a method of treating cancer in a subject in need thereof comprising administering a therapeutically effective amount of the peptides of the present invention or of the conjugates of the present invention. According to one embodiment, the method of treating cancer comprises administering a pharmaceutical composition comprising said peptides or said conjugates. According to one embodiment, the peptide is selected from a peptide comprising or consisting of SEQ ID NO: 1, a peptide comprising or consisting of SEQ ID NO: 2, a peptide comprising or consisting of SEQ ID NO: 3, a peptide comprising or consisting of SEQ ID NO: 4 and an analog of said peptides. According to another embodiment, the conjugate is a conjugate of said peptides. According to some embodiments, the method comprises administering the pharmaceutical composition of the present invention comprising said peptides or said conjugates.

According to a further aspect, the present invention provides an isolated polynucleotide comprising a sequence encoding the peptide or analog of the present invention. According to one embodiment, the peptide is selected from a peptide comprising or consisting of SEQ ID NO: 1, a peptide comprising or consisting of SEQ ID NO: 2, a peptide comprising or consisting of SEQ ID NO: 3, and a peptide comprising or consisting of SEQ ID NO: 4. According to another embodiment, the analog is an analog of said peptides.

According to further aspect, the present invention provides an isolated polynucleotide comprising a sequence encoding for a polypeptide comprising (i) at least one copy of SEQ ID NO: 1; (ii) at least one copy of SEQ ID NO: 2; (iii) at least one copy of SEQ ID NO: 3, 4 or combination thereof.

According to yet another aspect, the present invention provides a nucleic acid construct comprising the polynucleotide of the present invention. According to one embodiment, the polynucleotide is operably linked to a promoter.

According to certain aspects, the present invention provides a vector comprising at least one polynucleotide or at least one nucleic acid construct of the present invention.

According to a further aspect, the present invention provides a cell comprising at least one polynucleotide or at least one nucleic acid construct of the present invention.

BRIEF DESCRIPTION OF THE FIGURES

FIGS. 4-7 show the effect of PEG-E13.3-toxin construct on A431 and MCF-7 cells:

FIG. 4—control (no treatment)

FIG. 5 shows the effect of PEG-E13.3-BIM (FIG. 5A-C) construct and of PEG-E13.3-Tox1-Tox2 (FIG. 5D-5F) on A431 cells at different concentrations: 1 µM (FIGS. 5A and 5D), 3 µM (FIGS. 5B and 5E) and 8 µM (FIGS. 5C and 5F). The pictures were taken 48 hours after the treatment.

FIG. 6 shows the effect of PEG-E13.3-BIM (FIG. 6A-C) construct and of PEG-E13.3-Tox1-Tox2 (FIG. 6D-6F) on MCF-7 cells at different concentrations: 1 µM (FIGS. 6A and 6D), 3 µM (FIGS. 6B and 6E) and 8 µM (FIGS. 6C and 6F). The pictures were taken 48 hours after the treatment.

FIG. 7 shows treatment of A431 cells (FIG. 7A-7C) and MCF-7 (FIG. 7D-7F) with a complex of PEG-BIM (without E13.3) at different concentrations: 1 µM (FIGS. 7A and 6D), 3 µM (FIGS. 7B and 7E) and 8 µM (FIGS. 7C and 7F). The pictures were taken 48 hours after the treatment.

FIG. 9 shows effect of treatment of A-549 cells with PEG-E13.3-(PD-L1-GR)-Tox1-Tox2: 3 and 10 µM (FIGS. 9C and 9D, respectively) or PEG-E13.3-(PD-L1-GR)-BIM 10 µM (FIG. 9E).

DETAILED DESCRIPTION OF THE INVENTION

Figure 1:
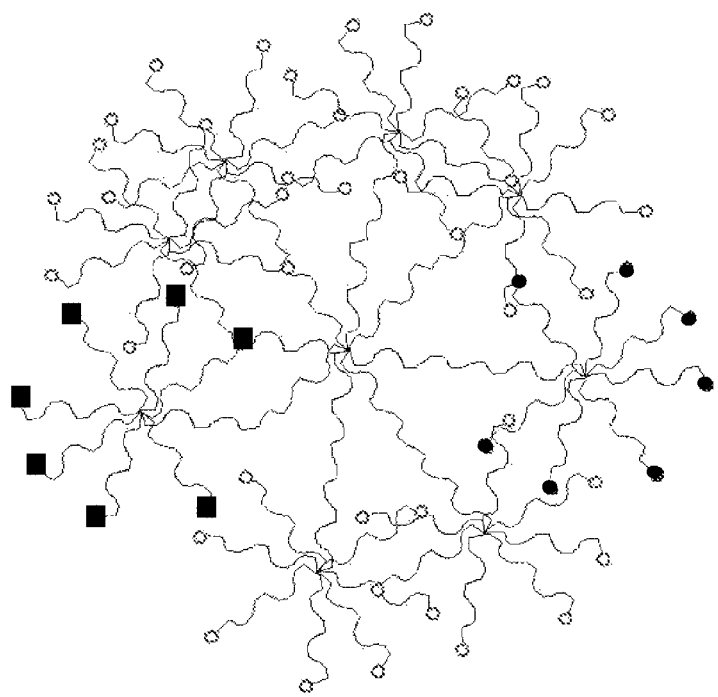
FIG. 1 shows schematic structure of a multi-arm-PEG complex loaded with two targeting molecules such as E13.3 and PL-L1-GR peptides (solid circles and squares) and a toxin (hollow circles) such as Tox1 and/or Tox2.

The present invention relates to therapeutic constructs comprising a plurality of multi-target peptides and at least one toxin moiety. In particular, a construct according to the present invention comprises a plurality of peptides each directed against a different cell-target. Peptides contained in a construct according to the invention are capable of binding, blocking, inhibiting, or activating at least two different antigens expressed on the membrane of cancer cells. The present invention provides, according to one aspect, a construct comprising at least two different peptides binding to at least two different extracellular tumor antigens, and at least one toxin, wherein the peptides and the toxin are covalently bound directly or through a carrier.

The term "peptide" refers to a short chain of amino acid residues linked by peptide bonds, i.e., a covalent bond formed between the carboxyl group of one amino acid and an amino group of an adjacent amino acid. The term "peptide" refers to short sequences having up to 50 amino acids. A chain of amino acids monomers longer than 50 amino acid is referred as a "polypeptide". Such polypeptides, when having more than 50 amino acid residues, can also be classified as proteins, more particularly, proteins of low or medium molecular weight.

The term "peptide" encompasses also the term "peptide analog". The term "peptide analog" and "analog" are used herein interchangeably and refer to an analog of a peptide having at least 70% identity with the original peptide, wherein the analog retains the activity of the original peptide. Thus, the terms "analog" and "active analog" may be used interchangeably. The term ""analog" refer to a peptide which contains substitutions, rearrangements, deletions, additions and/or chemical modifications in the amino acid sequence of the parent peptide. The term "analog" refers also to analogs of peptide toxins, i.e. toxins being peptides. According to some embodiments, the peptide analog has at least 80%, at least 90% or at least 95% sequence identity to the original peptide. According to one embodiment, the analog has about 70% to about 95%, about 80% to about 90% or about 85% to about 95% sequence identity to the original peptide. According to some embodiments, the analog of the present invention comprises the sequence of the original peptide in which 1, 2, 3, 4, or 5 substitutions were made.

The substitutions of the amino acids may be conservative or non-conservative substitution. The non-conservative substitution encompasses substitution of one amino acid by any other amino acid. In one particular embodiment, the amino acid is substituted by a non-natural amino acid.

The term "amino acid" as used herein refers to an organic compound comprising both amine and carboxylic acid functional groups, which may be either a natural or non-natural amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine. According to one embodiment, the substitution is substitution with a non-natural amino acid.

According to some embodiments, the term "analog" encompasses also the term "conservative analog".

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. One of skill will recognize that individual substitutions, is a "conservatively modified analog" where the alteration results in the substitution of an amino acid with a chemically similar amino acid. Conservative substitution tables providing functionally similar amino acids are well known in the art. One typical example of conservative substitution is provided below.

The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). In other embodiments, the conservative substitution encompass substitution with a chemically similar non-natural amino acid.

Thus, in some embodiments, the analog is a conservative analog of the peptide. According to some embodiments, the conservative analog of the present invention comprises the sequence of the original peptide in which 1, 2, 3, 4, or 5 conservative substitutions were made. According to another embodiment, the analog consists of the amino acid sequence of the original peptide in which 1, 2 or 3 conservative substitution were made. Thus, the analog consists of the amino acid sequence of the original peptide with 1, 2 or 3 conservative substitutions.

The term "peptide" encompasses also the term "peptide fragment". The term "fragment" refers to a fragment of the original peptide or of an analog thereof wherein said fragment retains the activity of the original peptide or analog. Thus, the terms "fragment" and "active fragment" may be used interchangeably. According to some embodiments, the fragment consists of at least 6, at least 8, at least 9, or at least 10 consecutive amino acids of the original sequence or of an analog thereof. According to one embodiment, the fragment consists of 6 to 11, 7 to 10 or 8 to 9 consecutive amino acids of the original sequence or analog thereof.

The peptides, analogs and fragments of present invention may be produced by any method known in the art, including recombinant (for peptides consisting of genetically encoded amino acids) and synthetic methods. Synthetic methods include exclusive solid phase synthesis, partial solid phase synthesis, fragment condensation, or classical solution synthesis. Solid phase peptide synthesis procedures are well known to one skilled in the art. Synthetic methods to produce peptides include but are not limited to FMOC solid phase peptide synthesis described, for example in Fields G. B., Noble R., Int. J. Pept. Protein Res., 35: 161-214, 1990. Methods for synthesizing peptides on PEG are described for example in DeNardo et al. Ibid.

In some embodiments, synthetic peptides are purified by preparative high performance liquid chromatography and the peptide sequence is confirmed via amino acid sequencing by methods known to one skilled in the art.

In some embodiments, recombinant protein techniques, well known in the art, are used to generate peptides and peptide multimers (consisting of genetically encoded amino acids) of the present invention.

As used herein, the term "toxin" refers to a peptide or polypeptide substance which is poisonous, harmful or toxic (cytotoxic) to mammalian cells, such as human cells. The toxin according to the present invention may be originated from living organism such as a microorganism, plant, or higher organism, or which may be synthetically prepared, produced, or designed using any known technique, for example as described in WO 2007/010525. The toxin typically interacts with cellular biological macromolecules such as enzymes and receptors to mediate its effect. The term encompasses biologically active subunits or fragments of a toxin. According to certain embodiments, the toxin is a peptide toxin, consisting of up to 50 amino acids. According to some embodiments, the toxin being a peptide may be a cyclic peptide. For the sake of clarity, the toxin being a cyclic peptide is referred as a "cyclotoxin" or "cyclic toxin". Within a construct of the present invention, a toxin moiety confers at least some of its properties to the construct, and the construct mediates poisonous or harmful effects on the target cells. None limiting examples of peptide toxin include cyanobacteria toxins such as Microcystins and Nodularins, ProTx-I and ProTx-II toxins, snake venom-derived disintegrins such as Viperistatin or fragments thereof, and Hm-1 and Hm-2 toxins.

The terms "carrier" refers to any molecule that covalently binds or capable of binding to the at least two different peptides and/or a toxin. Several possible binding arrangements are encompassed. According to one embodiment, one peptide and one toxin are bound via a carrier and the second peptide is bound directly to the first peptide or to the toxin. According to another embodiment, two peptides are bound via a carrier, and the toxin is bound to one of the peptides. According to a further embodiment, all peptides and toxin(s) are covalently bound to a carrier.

According to any one of the above embodiment, the peptides and/or the toxin(s) are bound via a linker. The terms "linker" and "spacer" are used herein interchangeably and refer to any molecule that covalently binds and therefore linking two molecules. Non-limiting examples of the linker are amino acids, peptides, or any other organic substance that can be used to allow distance between two linked molecules.

As used herein, the terms "target" and "cell target" refer to molecules found on cancer cells that may be a marker of cancer cell and may be involved in cancer cell growth, proliferation, survival and metastasis development. Particular examples of targets include cell-surface proteins, which upon binding to their counterparts, such as ligands, initiate a cascade that promotes tumor growth and development. A target according to the present invention is optionally highly expressed on cancer cells and not found, or found in substantially lower levels, on normal non-cancerous cells. The term "target" encompass therefore the term "extracellular tumor antigen". The term "tumor antigen" or "extracellular tumor antigen" are used herein interchangeably and include both tumor associated antigens (TAAs) and tumor specific antigens (TSAs). A tumor-associated antigen means an antigen that is expressed on the surface of a tumor cell in higher amounts than is observed on normal cells or an antigen that is expressed on normal cells during fetal development. A tumor specific antigen is an antigen that is unique to tumor cells and is not expressed on normal cells. The term tumor antigen includes TAAs or TSAs that have been already identified and those that have yet to be identified and includes fragments, epitopes and any and all modifications to the tumor antigens.

As used herein, the term "cell-targeting", when referring to a moiety, particularly a peptide, that is part of a construct of the present invention, indicates that the peptide provides cell-, tissue- or organ-specific targeting. In particular, a cell-targeting peptide specifically recognizes and binds a cell target on cancer cells. By virtue of its binding, the cell-targeting peptide directs the entire construct to the cancerous tissue, to facilitate specific killing/inhibition of cancerous cells. Killing/inhibition of cancerous cells is typically affected via the toxin present in the construct, but in some embodiments it may be affected directly by the binding of the cell-targeting peptide.

In one embodiment, the present invention provides a construct comprising at least two different peptides binding to at least two different extracellular tumor antigens, and at least one toxin, wherein the peptides and the toxin are covalently connected directly or through a carrier. According to some embodiments, the construct comprises at least 3 different said peptides. According to other embodiments, the construct comprises at least 4 different said peptides. According to certain embodiments, the construct comprises two or more different peptides binding to two or more different extracellular tumor antigens. According to one embodiment, the construct comprises three or more different peptides binding to three or more different extracellular tumor antigens. According to another embodiment, the construct comprises 4 or more different peptides binding to 4 or more different extracellular tumor antigens.

Not limiting examples of the extracellular tumor antigens are EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR, thus according to one embodiment, at least one of the peptides binds specifically to one such extracellular tumor antigen.

According to some embodiments, at least one of the peptides binds specifically to an extracellular tumor antigens selected from Epidermal Growth Factor Receptor (EGFR) or programmed death-ligand 1 (PD-L1). The terms "PD-L1" and "human PD-L1" are used herein interchangeably. The terms "EGFR" and "human EGFR" are used herein interchangeably.

According to other embodiments, the other one of the at least two peptides binds specifically to an extracellular tumor antigen selected from the group consisting of EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR.

According to a further embodiment, at least one of the peptides binds specifically to EGFR or PD-L1 and the other one of the at least two peptides binds specifically to an extracellular tumor antigen selected from EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR.

According to any one of the above embodiments, the peptide consists of 5 to 30 amino acids. According to other embodiments, each peptide consists of 6 to 25 amino acids. According to yet other embodiments, each peptide consists of 7 to 20 amino acids. According to some embodiments, each peptide consists of 8, 9, 10, 11, 12, 13, 14, 15, 16, 17, 18, 19 or 20 amino acids. Each possibility represents a separate embodiment of the invention.

According to any one of the above embodiments, the peptide of the present invention is a cyclic peptide. The terms "cyclic peptide" and "cyclopeptide" are used herein interchangeably and refer to a peptide having an intramolecular bond between two non-adjacent amino acids. The cyclization can be effected through a covalent or non-covalent bond. Intramolecular bonds include, but are not limited to, backbone to backbone, side-chain to backbone and side-chain to side-chain bonds. According to some embodiments, the cyclization occurs between the cysteines of the peptide, analogs of fragments. According to other embodiments, the cyclization occurs between the N-terminal and C-terminal amino acids.

According to any one of the above embodiments, the construct comprises two or more peptides binding to two or more different extracellular tumor antigens. According to some embodiments, the construct comprises 2 to 10 different peptides binding to 2 to 10 different extracellular tumor antigens. According to other embodiments, the construct comprises 3 to 8, 3 to 10, or 4 to 6 different peptides. According to one embodiment, the construct comprises 2 different peptides binding to 2 different extracellular tumor antigens. According to a further embodiment, the construct comprises 3 different peptides binding to 3 different extracellular tumor antigens. According to another embodiment, the construct comprises 4 different peptides binding to 4 different extracellular tumor antigens. According to certain embodiments, the construct comprises 5, 6, 7 or 8 different peptides binding to 5, 6, 7 or 8 different extracellular tumor antigens, respectively. According to some embodiments, at least one of the peptides bind specifically to EGFR or PD-L1.

According to one embodiment, the extracellular tumor antagonist is human EGFR. Thus, according to one embodiment, at least one of the peptides binds specifically to EGFR. According to some embodiments, the peptide is a peptide having the amino sequence set forth in SEQ ID NO: 1 (CHPGDKQEDPNCLQADK). According to other embodiments, the peptide is a peptide consisting of the amino sequence set forth in SEQ ID NO: 1. According to some such embodiments, the peptide comprising or consisting of SEQ ID NO: 2 is cyclic.

According to another embodiment, the peptide is an analog of the peptide having SEQ ID NO: 1. In yet another embodiment, the peptide is a conservative analog of SEQ ID NO: 1. According to some embodiments, the peptide is an analog having at least 70%, at least 75%, at least 80%, at least 85, at least 90% or at least 95% identity to SEQ ID NO: 1. According to other embodiments, the analog is a peptide having 70% to 95%, 75% to 90%, or 80% to 85% sequence identity to SEQ ID NO: 1. According to some embodiments, the analog of SEQ ID NO: 1 is a conservative analog of SEQ ID NO: 1 that has 1, 2, 3, 4 or 5 conservative substitutions.

According to a further embodiment, the peptide is a fragment of SEQ ID NO: 1 or of an analog thereof. According to some embodiments, the fragment consists of at least 6, at least 8, at least 10, at least 12, at least 14 or at least 16 consecutive amino acids of SEQ ID NO: 1 or analog thereof. According to one embodiment, the fragment consists of 5 to 16, 6 to 14, 7 to 13, 8 to 12, 8 to 12, or 9 to 11 consecutive amino acids of SEQ ID NO: 1 or analog thereof. In another embodiment, the peptide fragment consists of 6 to 16, 8 to 14 or 10 to 12 consecutive amino acids of SEQ ID NO: 1

According to any one of the aspects and embodiments of the invention, the terms "peptide comprising the amino acid sequence set forth in SEQ ID NO: X", "peptide comprising SEQ ID NO: X" and "peptide having SEQ ID NO: X" are used herein interchangeably. The terms "peptide consisting of the amino acid sequence set forth in SEQ ID NO: X", "peptide consisting of SEQ ID NO: X" and "peptide of SEQ ID NO: X" are used herein interchangeably.

According to one embodiment, the extracellular tumor antagonist is human PD-L1. Thus according to one embodiment, at least one of the peptides binds specifically to PD-L1. According to some embodiments, the peptide is a peptide having the amino sequence set forth in SEQ ID NO: 2 (CEGLPADWAAAC). According to certain embodiments, the peptide is a peptide consisting of SEQ ID NO: 2. According to some such embodiments, the peptide comprising or consisting of SEQ ID NO: 2 is cyclic.

According to another embodiment, the peptide is an analog of SEQ ID NO: 2. In yet another embodiment, the peptide is a conservative variant of SEQ ID NO: 2. According to some embodiments, the analog is a peptide having at least 70%, at least 75%, at least 80%, at least 85%, at least 90% or at least 95% identity to SEQ ID NO: 2. According to other embodiments, the analog is a peptide having 70% to 95%, 75% to 90%, or 80% to 85% identity to SEQ ID NO: 2. According to some embodiments, the analog is a conservative analog of SEQ ID NO: 2 that has 1, 2, 3, 4 or 5 conservative substitutions.

According to a further embodiment, the peptide is a fragment of SEQ ID NO: 2 or of an analog thereof. According to some embodiments, the fragment consists as least 6, at least 7, at least 8, at least 9, at least 10 or 11 consecutive amino acids of SEQ ID NO: 2 or analog thereof. According to one embodiment, the fragment consists of 5 to 16, 6 to 14, 7 to 13, 8 to 12, 8 to 12, or 9 to 11 consecutive amino acids of SEQ ID NO: 1 or analog thereof. In another embodiment, the peptide fragment consists of 6 to 16, 8 to 14 or 10 to 12 consecutive amino acids of SEQ ID NO: 1

According to any one of the above embodiments, the peptides comprising or consisting of SEQ ID NO: 1 or 2, analogs of fragments thereof are cyclic peptides, analogs or fragments.

According to some embodiments, at least one of the peptides binds specifically to EGFR, and at least one of the peptides binds specifically to PD-L1. According to some embodiments, the construct of the present invention has a synergistic cytotoxicity. The term "synergistic cytotoxicity" as used herein refers to a condition in which the cytotoxicity of the construct comprising two or more tumor antigen targeting peptides is higher that the cytotoxicity of 2 or more constructs, respectively, when each such construct comprises only one of the targeting peptides. Thus, the cytotoxicity of a construct comprising PD-L1 and EGFR targeting peptides is higher that a cytotoxicity of two constructs each comprising PD-L1 or EGFR targeting peptides (considering the concentrations of the constructs). According to some embodiments, the construct comprises one peptide that binds specifically to EGFR and another peptide that binds specifically to PD-L1. According to one embodiment, the peptide that binds to EGFR is a peptide having SEQ ID NO: 1, analog or fragment thereof. According to another embodiment, the peptide that binds specifically to PD-L1 is a peptide having SEQ ID NO: 2, analog or fragment thereof. According to certain embodiments, the construct comprises a peptide having SEQ ID NO:1, analog or fragment thereof and a peptide having SEQ ID NO: 2, analog or fragment thereof. According to certain embodiments, the construct comprises a peptide having SEQ ID NO: 1 and a peptide having SEQ ID NO: 2. According to certain embodiments, the construct comprises a peptide of SEQ ID NO: 1 and a peptide of SEQ ID NO: 2. According to some such embodiments, the peptides comprising or consisting of SEQ ID NO: 1 or 2, analogs of fragments thereof are cyclic peptides, analogs or fragments. According to some embodiments, the construct of the present invention has a synergistic cytotoxicity.

According to any one of the above embodiments, the construct of the present invention comprises multiple copies of at least one of the different peptides.

According to other embodiments, the construct of the present invention comprises multiple copies of each one of the at least two of the different peptides. According to another embodiment, the construct comprises multiple copies of each one of the peptides.

The term "different peptides" refer to peptides binding to different binding site and not to two copies of the same peptide.

According to some embodiments, the construct comprises from 2 to 100, 3 to 90, 4 to 60, 5 to 50, 6 to 40, 7 to 35, 8 to 30, 9 to 25 or 10 to 20 copies of a peptide. According to one embodiment, the construct comprises 2 to 50 copies of a peptide. According to another embodiment, the construct comprises from 7 to 56, from 14 to 48, from 21 to 42 from 28 to 35, from 7 to 21 copies of a peptide. According to other embodiments, the construct comprises 2 to 100, 3 to 90, 4 to 60, 5 to 50, 6 to 40, 7 to 35, 8 to 30, 9 to 25 or 10 to 20 copies of each one of the two different peptides. According to one embodiment, the construct comprises 2 to 50 copies of each one of the two different peptides. According to some embodiments, the construct comprises from 7 to 56, from 14 to 48, from 21 to 42 from 28 to 35, from 7 to 21 copies of each one of the two different peptides. In certain embodiments, the contract comprises from 7 or from 14 to 28 copies of each one of the 3, 4 or 5 different peptides.

According to some embodiments, the construct comprises multiple copies of a peptide that binds specifically to EGFR and/or multiple copies of a peptide that binds specifically to PD-L1. According to some other embodiments, the construct comprises multiple copies of the peptide having the SEQ ID NO: 1, analog or fragment thereof and multiple copies of the peptide having the SEQ ID NO: 2, analog or fragment thereof. According to some embodiments, the construct comprises from 2 to 100, 3 to 90, 4 to 60, 5 to 50, 6 to 40, 7 to 35, 8 to 30, 9 to 25 or 10 to 20 copies of the peptide having SEQ ID NO: 1, analog or fragment thereof and/or of the peptide having the SEQ ID NO: 2, analog or fragment thereof. According to one embodiment, the construct comprises 2 to 50 copies of the peptide having SEQ ID NO: 1, analog or fragment thereof and/or of the peptide having the SEQ ID NO: 2, analog or fragment thereof. According to some embodiments, the construct comprises from 7 to 56, from 14 to 48, from 21 to 42 from 28 to 35, or from 7 to 21 copies of the peptide having the SEQ ID NO: 1. According to some embodiments, the construct comprises from 7 to 56, from 14 to 48, from 21 to 42 from 28 to 35, or from 7 to 21 copies of the peptide having the SEQ ID NO: 2. According to some embodiments, the construct comprises from 7 to 56, from 14 to 48, from 21 to 42 from 28 to 35, or from 7 to 21 copies of the each one of the peptide having the SEQ ID NO: 1 and 2. According to any one of the above embodiments, the peptides comprising or consisting of SEQ ID NO: 1 or 2, analogs of fragments thereof are cyclic peptides, analogs or fragments.

According to any one of the above embodiments, the toxin is selected from a peptide toxin, polypeptide toxin or peptide toxin.

According to some embodiments, the toxin is selected from the group consisting of a toxin binding to a eukaryotic elongation factor 2 or analog of that toxins, BIM-BH3 toxin, Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, and cyanotoxin. According to some embodiments, the BIM-BH3 toxin consists of the amino acid sequence MRPEIWIAQELRRIGDEFNA (SEQ ID NO: 5).

According to some embodiments, the toxin binding to eukaryotic elongation factor 2 is a toxin having the amino acid sequence selected from CSARWGPTMPWC (as set forth in SEQ ID NO: 3) or CRRGSRASGAHC (as set forth in SEQ ID NO: 4), or an analog thereof.

According to another embodiment, the toxin is selected from the group consisting a toxin having SEQ ID NO: 3, a toxin having SEQ ID NO: 4, a toxin of SEQ ID NO: 5 (BIM-BH3 toxin), Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, and cyanotoxin.

According to some embodiments, the toxin is a toxin comprising SEQ ID NO: 3. According to other embodiments, the toxin is a toxin comprising SEQ ID NO: 4. According to another embodiment, the toxin consists of SEQ ID NO: 3. According to yet another embodiment, the toxin consists of SEQ ID NO: 4. According to one embodiment, the toxin consists of SEQ ID NO: 5. According to some embodiments, the toxin is an analog of a toxin comprising the SEQ ID NO: 3 or 4. According to certain embodiments, the toxin is an analog of a toxin consisting of the SEQ ID NO: 3 or 4. According to some such embodiments, the toxin or analog thereof is cyclic toxin or analog.

According to some embodiments, the analog of a toxin comprising SEQ ID NO: 3 has at least 70%, at least 75%, at least 80%, at least 85, at least 90% or at least 95% identity to SEQ ID NO: 3. According to other embodiments, the analog is a peptide having 70% to 95%, 75% to 90%, or 80% to 85% sequence identity to SEQ ID NO: 3. According to some embodiments, the analog is a conservative analog of SEQ ID NO: 3 that has 1, 2, 3, 4 or 5 conservative substitutions.

According to some embodiments, the analog of a toxin comprising SEQ ID NO: 4 has at least 70%, at least 75%, at least 80%, at least 85, at least 90% or at least 95% identity to SEQ ID NO: 4. According to other embodiments, the analog is a peptide having 70% to 95%, 75% to 90%, or 80% to 85% identity to SEQ ID NO: 4. According to some embodiments, the analog is a conservative analog of SEQ ID NO: 4 that has 1, 2, 3, 4 or 5 conservative substitutions.

According to some such embodiments, the toxins binding to eEF2, and in particular the toxins comprising or consisting of SEQ ID NO: 3, or, analogs or fragments thereof have cyclic structure, i.e. being cyclotoxins.

According to some embodiments, the construct comprises 2 to 10 different toxins. According to one embodiment, the construct comprises 2 different toxins. According to another embodiment, the construct comprises 3 different toxins. According to a further embodiment, the construct comprises 4, 5, 6, 7, 8, 9 or 10 different toxins.

According to certain embodiments, the construct comprises a toxin having the amino acid SEQ ID NO: 3 and a toxin having the amino acid SEQ ID NO: 4.

According some embodiments, the construct of the present invention comprises multiple copies of at least one of the toxins. According to other embodiment, the construct comprises multiple copies of at least two toxins.

According to some embodiments, the construct comprises multiple copies of at least one toxin having SEQ ID NO: 3 or 4. According to other embodiments, the construct comprises multiple copies of at least one toxin having SEQ ID NO: 3, or 4.

According to some embodiments, the construct comprises from 2 to 100, 3 to 90, 4 to 60, 5 to 50, 6 to 40, 7 to 35, 8 to 30, 9 to 25 or 10 to 20 copies of a toxin. According to one embodiment, the construct comprises 2 to 50 copies of a toxin. According to another embodiment, the construct comprises from 7 to 56, from 14 to 48, from 21 to 42 from 28 to 35, from 7 to 21 copies of a toxin. According to other embodiments, the construct comprises 2 to 100, 3 to 90, 4 to 60, 5 to 50, 6 to 40, 7 to 35, 8 to 30, 9 to 25 or 10 to 20 copies of each one of two different toxins. According to one embodiment, the construct comprises 2 to 50 copies of each one of two different toxins. According to some embodiments, the construct comprises from 7 to 56, from 14 to 48, from 21 to 42 from 28 to 35, from 7 to 21 copies of each one of two different toxins. In certain embodiments, the contract comprises from 7 or from 14 to 28 copies of each one of the 3, 4 or 5 different toxins.

According to some embodiments, the construct comprises from 2 to 100, 3 to 90, 4 to 60, 5 to 50, 6 to 40, 7 to 35, 8 to 30, 9 to 25, 2 to 50, or 10 to 20 copies of a toxin having SEQ ID NO: 3, analog or fragment thereof and/or of the toxin having the SEQ ID NO: 4, analog or fragment thereof. According to some embodiments, the construct comprises from 7 to 56, from 14 to 48, from 21 to 42 from 28 to 35, from 7 to 21 copies of the toxin having the SEQ ID NO: 3. According to some embodiments, the construct comprises from 7 to 56, from 14 to 48, from 21 to 42 from 28 to 35, from 7 to 21 copies of the toxin having the SEQ ID NO: 4. According to some embodiments, the construct comprises from 7 to 56, from 14 to 48, from 21 to 42 from 28 to 35, from 7 to 21 copies of the each one of the toxins having the SEQ ID NO: 3 and 4.

According to one embodiment, the molar ratio of the toxin having the amino acid SEQ ID NO: 3 to the toxin having the amino acid SEQ ID NO: 4 is about 0.1:1 to about 10:1. According to some embodiments, the ratio is about 0.2:1 to 8:1, about 0.4:1 to 6:1 about 0.5:1 to 5:1 about 0.6:1 to 4:1, about 0.8 to 1 to 2:1 or about 1:1. According to one embodiment, the molar ratio of the toxin having the amino acid SEQ ID NO: 3 to the toxin having the amino acid SEQ ID NO: 4 is 1:1.

According to some embodiments, the present invention provides a construct of the present invention comprising at least two different peptides binding to at least two different extracellular tumor antigens, and at least one toxin, wherein one of the peptides binds specifically to EGFR and one of the peptides binds specifically to PD-L1 and the toxin is selected from a toxin binding to a eukaryotic elongation factor 2, BIM-BH3 toxin having the amino acid sequence set forth in SEQ ID NO: 5, Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, cyanotoxin, and any combination thereof. According to some embodiments, the toxin is a toxin binding to eukaryotic elongation factor 2. According to some embodiments, the present invention provides a construct in which one of the peptides binds specifically to EGFR and one of the peptides binds specifically to PD-L1 and the toxin binds to a eukaryotic elongation factor 2 or the toxin of SEQ ID NO: 5. According to some embodiments, the peptides that binds specifically to EGFR is a peptide having SEQ ID NO:1, an analog or a fragment thereof, the peptide that binds specifically to PD-L1 is a peptide having SEQ ID NO: 2, an analog or a fragment thereof, and the toxin is selected from a toxin having SEQ ID NO: 3 or 4. According to some embodiments, the construct comprises multiple copies of (i) one peptide, (ii) two peptides, (iii) one toxin and/or (iv) two toxins. According to some embodiments, the construct comprises multiple copies of: (i) a peptide having SEQ ID NO:1, an analog or a fragment thereof, (ii) a peptide having SEQ ID NO: 2, an analog or a fragment thereof, and (iii) a toxin selected from a toxin having SEQ ID NO: 3 or 4, or combination thereof. According to other embodiments, the construct comprises multiple copies of (i) a peptide of SEQ ID NO:1, (ii) a peptide of SEQ ID NO: 2, (iii) the toxin of SEQ ID NO: 3 or 4, or a combination thereof. According to other embodiments, the construct comprises multiple copies of each one of: (i) a peptide of SEQ ID NO: 1, (ii) a peptide of SEQ ID NO: 2, (iii) the toxin of SEQ ID NO: 3, and (iv) the toxin of SEQ ID NO: 4. According to some embodiments, the construct of the present invention has a synergistic cytotoxicity. According to some such embodiments, the peptides, analogs thereof or the fragments thereof and/or the toxins, the analogs thereof or the fragments thereof are cyclic peptides, analogs or the fragments and/or cyclic toxins, analogs of fragments thereof, respectively.

According to any one of the above embodiment, the peptides of the present invention are covalently bound to each other. According to one embodiment, the peptides and the toxins are bound directly, i.e. without a carrier. According to other embodiments, the peptides of the present invention are covalently bound through a carrier. According to one embodiment, the carrier is an organic scaffold, thus the peptides are covalently bound through a scaffold.

According to some embodiments, the scaffold is a peptidic scaffold. According to other embodiments, the peptidic scaffold connects the peptides to each other on a single location in the scaffold, or to a different location on a scaffold. Each possibility represents a separate embodiment of the invention. According to some embodiments, the scaffold comprises at least one Lysine (Lys) residue. According to other embodiments, the scaffold comprises at least three Lys residues. According to further embodiments, the at least three Lys residues are connected together by amide bonds to form a branched multimeric scaffold. According to some embodiments, at least one amide bond is formed between the epsilon amine of a Lys residue and the carboxy group of another Lys residue.

According to a particular embodiment, the construct comprises a molecule according to one of the schemes presented below, $$\begin{array}{c}
\text{Lys-peptide} \\
\text{Lys} \\
\text{X-Lys} \quad \text{Lys-peptide} \\
\text{Lys-peptide} \\
\text{Lys} \\
\text{Lys-peptide}
\end{array}
\quad
\begin{array}{c}
\text{peptide} \\
\text{Lys} \\
\text{peptide} \quad \text{X-Lys-Lys-Lys} \\
\text{peptide} \\
\text{Lys} \\
\text{peptide}
\end{array}
\quad
\begin{array}{c}
\text{peptide} \\
\text{Lys} \\
\text{peptide} \\
\text{peptide} \\
\text{Lys} \\
\text{peptide}
\end{array}$$

wherein X represents the peptide's and/or the toxin's C-terminal selected from carboxy acid, amide or alcohol group and optionally a linker or spacer, and peptide denotes a peptide according to the present invention, e.g. having 7-20 amino acids capable of binding to a cell-target. Each possibility represents a separate embodiment of the present invention.

According to some specific embodiments, at least one of the peptides and/or the toxin(s) is present in multiple copies. According to some embodiments, the multiple copies are linked thereby forming a multi-target peptide multimer. According to some embodiments, the peptide and/or the toxin(s) copies are linked through a linker. According to other embodiments, the peptides and/or the toxin(s) copies are linked directly. According to a further embodiments, the multimer comprises copies linked both directly and via a linker.

According to some embodiments, the construct comprises a peptide multimer comprising a plurality of cell-targeting peptides arranged in an alternating sequential polymeric structure $B(X_1X_2X_3 \ldots X_m)_nB$ or in a block copolymer structure $B(X_1)_{nZ}(X_2)_{nZ}(X_3)_nZ \ldots (X_m)_n$, wherein B is an optional sequence of 1-10 amino acid residues; n is at each occurrence independently an integer of 2-50; m is an integer of 3-50; each of $X_1, X_2 \ldots X_m$ is an identical or different peptide consisting of 5-30 amino acid residues; Z at each occurrence is a bond or a spacer of 1-4 amino acid residues. According to particular embodiments, n is at each occurrence independently an integer of 2-10; m is an integer of 3-10; each of $X_1, X_2 \ldots X_m$ is an identical or different peptide consisting of 7-20 amino acid residues; Z at each occurrence is a bond or a spacer of 1-4 amino acid residues. Each possibility represents a separate embodiment of the present invention.

According to some embodiments, the peptide multimer comprises 2-8 different or identical peptides. According to a particular embodiment, the peptide multimer comprises 4-10 copies of a single peptide sequence. According to yet other embodiments, the peptide multimer consists of 2-10, 3-9, 4-8, or 10-100 different or identical peptides. Each possibility represents a separate embodiment of the present invention.

According to other embodiments, the scaffold comprises or formed from a polyethylene glycol (PEG) molecule(s) or a modified PEG molecule(s). According to certain embodiments, the scaffold comprises a branched PEG molecule. According to some embodiments, the branched molecule comprises at least two sites available to bind a peptide of the present invention. According to other embodiments, the scaffold comprises from 2 to 100, 3 to 90, 4 to 60, 5 to 50, 6 to 40, 7 to 35, 8 to 30, 9 to 25 or 10 to 20, or 2 to 50 sites available to bind a peptide. According to one embodiment, the construct comprises from 7 to 56, from 14 to 48, from 21 to 42 from 28 to 35, from 7 to 21 sites available to bind a peptide. According to certain embodiment, the scaffold comprises 8 or 56 sites available to bind a peptide. According to further embodiments, the scaffold comprises 42 or 49 to 56 sites available for binding a peptide.

According to some embodiments, the PEG molecule is a branched molecule, comprising at least two separate connections to a peptide. According to some embodiments, the PEG has 8 binding sites. According to other embodiments, the PEG is bound to additional PEG molecules. According to certain embodiments, multiple PEG molecules are bound to provide a multi-armed PEG molecule. According to some embodiments, eight 8-armed PEG molecules are abound to one central 8-armed PEG molecule to provide one PEG molecules with 56 sites capable of binding the peptides of the toxins of the present invention. According certain embodiments, the peptides are connected to the PEG scaffold through amide bonds formed between amino groups of an $NH_2$-PEG molecule. According to yet other embodiments, at least one peptide is connected to PEG scaffold though a Lys residue.

According to some embodiments, the peptides are bound to a PEG scaffold though a Lys residue.

According to some embodiments, the present invention provides a construct in which at least one of the peptides bound to PEG scaffold binds specifically to an extracellular tumor antigen selected from EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR. According to certain embodiments, at least one of the peptides bound to PEG scaffold binds specifically to EGFR or PD-L1. According to some embodiments, the peptide that binds specifically to EGFR and the peptide that binds specifically to PD-L1 are both bound to the scaffold. According to one embodiment, the peptide that binds to EGFR is a peptide having SEQ ID NO: 1, analog or fragment thereof. According to another embodiment, the peptide that binds specifically to PD-L1 is a peptide having SEQ ID NO: 2, analog or fragment thereof. According to certain embodiments, the construct comprises the peptide having SEQ ID NO: 1, analog or fragment thereof and a peptide having SEQ ID NO: 2, analog or fragment thereof both bound to the scaffold. According to certain embodiments, the construct comprises a peptide having SEQ ID NO: 1 and peptide having SEQ ID NO: 2 bound to the scaffold. According to certain embodiments, the construct comprises a peptide of SEQ ID NO: 1 and a peptide of SEQ ID NO: 2 bound to the scaffold. According to some such embodiments, the peptides comprising or consisting of SEQ ID NO: 1 or 2, analogs of fragments thereof are cyclic peptides, analogs or fragments.

According to some embodiments, the present invention provides a construct, wherein the scaffold is bound to multiple copies of at least one of the peptides. According to some embodiments, the scaffold is bound to multiple copies of each of the at least two of the peptides. According to certain embodiments, at least one of the peptides that is bound to PEG scaffold binds specifically to EGFR or PD-L1. According to some embodiments, the scaffold is bound to multiple copies of a peptide that binds specifically to EGFR. According to other embodiments, the scaffold is bound to multiple copies of a peptide that binds specifically to PD-L1. According to a further embodiment, the scaffold is bound to multiple copies of a peptide that binds specifically to EGFR and to multiple copies of a peptide that binds specifically to PD-L1. According to one embodiment, the peptide that binds to EGFR is a peptide having SEQ ID NO: 1, analog or fragment thereof. According to another embodiment, the peptide that binds specifically to PD-L1 is peptide having SEQ ID NO: 2, analog or fragment thereof. According to one embodiment, the scaffold is bound to multiple copies of the peptide having SEQ ID NO: 1 and to multiple copies of the peptide having SEQ ID NO: 2. According to some such embodiments, the peptides comprising or consisting of SEQ ID NO: 1 or 2, analogs of fragments thereof are cyclic peptides, analogs or fragments.

According to some embodiments, the scaffold comprises a carbohydrate moiety.

According to other embodiments, the toxin is bound to a carrier. The carrier may be as described herein above. Thus, according to one embodiment, the carrier is a scaffold. According to certain embodiments, the carrier is a peptidic scaffold.

According to other embodiments, the scaffold is PEG scaffold, i.e. formed from PEG. According to certain embodiments, the scaffold comprises a branched PEG molecule. According to some embodiments, the branched molecule comprises at least one available site to bind a toxin.

According to other embodiments, the scaffold comprises from 2 to 100, 3 to 90, 4 to 60, 5 to 50, 6 to 40, 7 to 35, 8 to 30, 9 to 25 or 10 to 20, or 2 to 50 sites available to bind a toxin. According to one embodiment, the construct comprises from 7 to 56, from 14 to 48, from 21 to 42 from 28 to 35, from 7 to 21 sites available to bind a toxin. According to certain embodiment, the scaffold comprises 8 or 56, or 42 or 49 to 56 sites available for bind a toxin.

According to some embodiments, the present invention provides as a construct, wherein the PEG scaffold is bound to multiple copies of at least one toxin. According to some embodiments, the present invention provides a construct, where the scaffold is bound to multiple copies of at least two toxins. According to some embodiments, the toxin is selected from the groups consisting of a toxin having SEQ ID NO: 3, a toxin having SEQ ID NO: 4, a toxin having SEQ ID NO: 5 (BIM-BH3 toxin), Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, cyanotoxin, and any combination thereof. According to some embodiments, the toxin is a toxin of SEQ ID NO: 3 or 4.

According to one embodiment, the PEG scaffold is bound to multiple copies of a toxin having SEQ ID NO: 3, an analog or fragment thereof. According to one embodiment, the PEG scaffold is bound to multiple copies of a toxin having SEQ ID NO: 4, an analog or fragment thereof. According to one embodiment, the PEG scaffold is bound to multiple copies of a toxin having SEQ ID NO: 5. According to one embodiment, the PEG scaffold is bound to multiple copies of a toxin of SEQ ID NO: 3 or 4.

According to one embodiment, the PEG scaffold is bound to multiple copies of each one of the toxins. According to one embodiment, the PEG scaffold is bound to multiple copies of a toxin having SEQ ID NO: 3 and to multiple copies of a toxin having SEQ ID NO: 4. According to one embodiment, the PEG scaffold is bound to multiple copies of the toxin of SEQ ID NO: 3 and to multiple copies of a toxin of SEQ ID NO: 4.

According to some such embodiments, the peptides comprising or consisting of SEQ ID NO: 1 or 2, analogs of fragments thereof are cyclic peptides, analogs or fragments. Additionally, the peptides comprising or consisting of SEQ ID NO: 3 or 4, analogs or fragments thereof are cyclic, i.e. cyclic toxins.

According to some embodiments, the present invention provides a construct comprising a PEG scaffold bound to at least two different peptides binding to at least two different extracellular tumor antigens, and to at least one toxin, wherein at least one of peptides binds specifically to the extracellular tumor antigens is selected from EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR.

According to some embodiments, the present invention provides a construct comprising at least two different peptides binding to at least two different extracellular tumor antigens and at least one toxin, wherein each of said peptides and toxin(s) is bound to a PEG scaffold and wherein at least one of peptides binds specifically to the extracellular tumor antigens selected from EGFR and PD-L1. According to one embodiment, one of the peptides binds specifically to EGFR and the another one of the at least two peptides binds specifically to an extracellular tumor antigen selected from the group consisting of PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR. According to another embodiment, one of the peptides binds specifically to PD-L1 and the another one of the at least two peptides binds specifically to an extracellular tumor antigen selected from the group consisting of EGFR, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR. According to other embodiments, one of the peptides binds specifically to EGFR and the other one of the at least two peptides binds specifically to PD-L1. According to some embodiments, the peptides binds specifically to EGFR is a peptide having SEQ ID NO:1, an analog or fragment thereof. According to some embodiments, the peptides binds specifically to PD-L1 is a peptide having SEQ ID NO:2, an analog or fragment thereof. According to some such embodiments, the peptide is a cyclopeptide. According to some embodiments, the toxin is selected from the groups consisting of a toxin having SEQ ID NO: 3, a toxin having SEQ ID NO: 4, a toxin having SEQ ID NO: 5 (BIM-BH3 toxin), Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, and cyanotoxin. According to some embodiments, the toxin is selected from the groups consisting of a toxin of SEQ ID NO: 3, a toxin of SEQ ID NO: 4, and a toxin of SEQ ID NO: 5. According to some embodiments, the scaffold is bound to 2, 3, or 4 different toxins. According to some embodiments, the PEG scaffold is bound to multiple copies of at least one of the peptides. According to other embodiments, the PEG scaffold is bound to multiple copies of each one of the at least two peptides. According to further embodiments, the PEG scaffold is bound to multiple copies of a toxin. According to certain embodiments, the PEG scaffold is bound to multiple copies of each one of two or more toxins. According to one embodiment, the scaffold is bound to multiple copies of a peptide having SEQ ID NO:1. According to another embodiment, the scaffold is bound to multiple copies of a peptide having SEQ ID NO:2. According to a further embodiment, the scaffold is bound to multiple copies of a peptide having SEQ ID NO: 1 and to multiple copies of a peptide having SEQ ID NO:2. According to one embodiment, the scaffold is bound to multiple copies of a toxin having SEQ ID NO: 3. According to another embodiment, the scaffold is bound to multiple copies of a toxin having SEQ ID NO: 4. According to a further embodiment, the PEG scaffold is bound to multiple copies of a toxin having SEQ ID NO: 3 and to multiple copies of a toxin having SEQ ID NO: 4. According to yet another embodiment, the PEG scaffold is bound to multiple copies of the toxin of SEQ ID NO: 3 and to multiple copies of a toxin of SEQ ID NO: 4. According to one embodiment, the molar ratio of the toxin having the amino acid SEQ ID NO: 3 or 5 to the toxin having the amino acid SEQ ID NO: 4 is about 0.1:1 to about 10:1 or 1:1. According to some embodiments, the construct of the present invention has a synergistic cytotoxicity.

According to some embodiments, the present invention provides a construct comprising multiple copies of a peptide having SEQ ID NO:1, multiple copies of a peptide having SEQ ID NO:2, multiple copies of a toxin having SEQ ID NO: 3 and multiple copies of a toxin having SEQ ID NO: 4, wherein each of the copies of the peptides and the toxins is bound to a PEG scaffold. According to some embodiments, the present invention provides a construct comprising a PEG scaffold bound to multiple copies of a peptide of SEQ ID NO:1, to multiple copies of a peptide of SEQ ID NO:2, multiple copies of a toxin of SEQ ID NO: 3 and to multiple copies of a toxin of SEQ ID NO: 4. According to one embodiment, the molar ratio of the toxin having the amino acid SEQ ID NO: 3 to the toxin having the amino acid SEQ ID NO: 4 is about 0.1:1 to about 10:1 or 1:1. According to some embodiments, the stoichiometric molar ratio between the peptide having SEQ ID NO:1, the peptide of SEQ ID NO:2, the toxin having SEQ ID NO: 3 and the toxin having SEQ ID NO: 3 is 1:1:3:3. According to other embodiments, the stoichiometric molar ratio between the peptide having SEQ ID NO:1, the peptide of SEQ ID NO:2, the toxin having SEQ ID NO: 3 and the toxin having SEQ ID NO: 4 is selected from 1:2:3:2, 1:2:2:3, 2:1:3:2, 2:1:2:3 and 2:2:2:2. In the abovementioned embodiments, the peptides comprising or consisting of SEQ ID NO: 1 or 2 are cyclopeptides and the toxins comprising or consisting of SEQ ID NO: 3 or 4 are cyclotoxins. According to some embodiments, the construct of the present invention has a synergistic cytotoxicity.

According to any one of the above embodiments, the peptides and/or the toxin(s) are bound directly or through a spacer. According to other embodiments, the peptides and/or the toxin(s) are bound to the carrier, e.g. to a scaffold, through a spacer. According to some specific embodiments, the spacer comprises at least one amino acid residue.

According to any one of the above embodiments, the construct further comprises a permeability-enhancing moiety. The permeability-enhancing moiety may be bound directly to a peptide and/or to a toxin, or may be bound to the scaffold, optionally via a spacer. The term "permeability-enhancing moiety" refers to any moiety known in the art to facilitate actively or passively or enhance permeability of the compound through body barriers or into the cells. Non-limitative examples of permeability-enhancing moiety include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides, nanoparticles and liposomes. The term "permeability" refers to the ability of an agent or substance to penetrate, pervade, or diffuse through a barrier, membrane, or a skin layer.

According to another aspect, the present invention provides a composition comprising a construct of the present invention. According to one embodiment, the composition is a pharmaceutical composition. Thus, in some embodiments, the present invention provides a pharmaceutical composition comprising a construct of the present invention and a pharmaceutically acceptable excipient. All definitions, terms and embodiments of previous aspects are explicitly encompassed by this aspect.

The term "pharmaceutical composition" as used herein refers to a composition comprising the construct of the present invention as disclosed herein optionally formulated with one or more pharmaceutically acceptable excipients.

Formulation of the pharmaceutical composition may be adjusted according to applications. In particular, the pharmaceutical composition may be formulated using a method known in the art so as to provide rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. Non-limiting examples of suitable excipients are example, water, saline, phosphate buffered saline (PBS), dextrose, glycerol, ethanol, or the like and combinations thereof. Other suitable carriers are well known to those skilled in the art. The use of such media and agents for pharmaceutically active substances is well known in the art. The compositions may contain other active compounds providing supplemental, additional, or enhanced therapeutic functions.

The constructs of the present invention could be, according to some embodiments, suspended in a sterile saline solution for therapeutic uses. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention from such a matrix depends upon the molecular weight of the molecule, the amount of the molecule within the matrix, and the size of dispersed particles.

The pharmaceutical composition of the present invention may be administered by any know method. The terms "administering" or "administration of" a substance, a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

According to some embodiments, the pharmaceutical composition is administered by an invasive mode of administration such as intramuscularly, intravenously, intra-arterially, intraarticulary or parenterally.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (polypeptide, polynucleotide, organic molecule etc.) age, body weight, sex, or conditions of the patient, it will be determined by the physician in the end. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

In one particular embodiment, the pharmaceutical composition of the present invention comprises a construct comprising at least two different peptides binding to at least two different extracellular tumor antigens, and at least one toxin, wherein the peptides and the toxin are covalently bound directly or through a carrier. According to some embodiments, at least one of the peptides binds specifically to an extracellular tumor antigens selected from EGFR and PD-L1. According to another embodiment, the other one of the at least two peptides binds specifically to an extracellular tumor antigen selected from the group consisting of EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR. According to certain embodiments, the construct comprises from 2 to 10 different peptides. According to some embodiments, at least one of the peptides binds specifically to EGFR, and at least one of the peptides binds specifically to PD-L1. According to one embodiment, the peptide that binds to EGFR is a peptide having SEQ ID NO: 1, analog or fragment thereof. According to another embodiment, the peptide that binds specifically to PD-L1 is a peptide having SEQ ID NO: 2, analog or fragment thereof. According to a further embodiment, the construct comprises a peptide having or consisting of SEQ ID NO: 1 and a peptide having or consisting of SEQ ID NO: 2. According to some embodiments, the pharmaceutical composition comprises a construct comprising multiple copies of one or of two of said peptides. According to some embodiments, the construct comprises from 7 to 56, from 14 to 48, from 21 to 42, from 28 to 35, or from 7 to 21 copies of the each one of the peptide having the SEQ ID NO: 1 and 2. According to some embodiments, the toxin is selected from the group consisting of a toxin binding to a eukaryotic elongation factor 2 or analog of that toxins, BIM-BH3 toxin, Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, and cyanotoxin. According to some embodiments, the BIM-BH3 toxin consists of SEQ ID NO: 5. According to certain embodiments, the toxin binding to eukaryotic elongation factor 2 is a toxin having the amino acid sequence selected from SEQ ID NO: 3 or 4, or an analog thereof. According to some embodiments, the construct comprises 2 to 10 different toxins. According to some embodiments, the construct comprises from 7 to 56, from 14 to 48, from 21 to 42 from 28 to 35, or from 7 to 21 copies of one or of two toxins. According to some embodiments, the construct comprises from 7 to 56, from 14 to 48, from 21 to 42 from 28 to 35, from 7 to 21 copies of the each one of the toxins having the SEQ ID NO: 3 or 4. According to some embodiments, the construct comprises from 7 to 56, from 14 to 48, from 21 to 42 from 28 to 35, from 7 to 21 copies of the each one of the toxins having the SEQ ID NO: 3 and 4. According to one embodiment, the molar ratio of the toxin having the amino acid SEQ ID NO: 3 to the toxin having the amino acid SEQ ID NO: 4 is about 0.1:1 to about 10:1 or about 1:1. According to some embodiments, the peptide(s) is a cyclic peptide(s) and the toxin(s) is a cyclic toxin(s).

According to some embodiments, the pharmaceutical composition of the present invention comprises a construct comprising a PEG scaffold, at least two different peptides binding to at least two different extracellular tumor antigens, and at least one toxin, wherein at least one of peptides binds specifically to the extracellular tumor antigens selected from EGFR and PD-L1, and each one of the peptides and the toxins are bound to the scaffold. According to other embodiments, one of the peptides binds specifically to EGFR and the other one to the at least two peptides binds specifically to PD-L1. According to some embodiments, the peptides binds specifically to EGFR is a peptide having SEQ ID NO:1, an analog or fragment thereof. According to some embodiments, the peptides binds specifically to PD-L1 is a peptide having SEQ ID NO:2, an analog or fragment thereof. According to some embodiments, the present invention provides a construct comprising a PEG scaffold, multiple copies of a peptide having SEQ ID NO:1, multiple copies of a peptide having SEQ ID NO:2, and multiple copies of a toxin having SEQ ID NO: 3, wherein each copy of each one of the peptides and each copy of the toxin are bound to the scaffold. According to one embodiment, the construct comprising a PEG scaffold, multiple copies of a peptide having SEQ ID NO:1, multiple copies of a peptide having SEQ ID NO:2, and multiple copies of a toxin having SEQ ID NO: 4, wherein each copy of each one of the peptides and each copy of the toxin are bound to the scaffold.

According to some embodiments, the present invention provides a construct comprising a PEG scaffold bound to multiple copies of a peptide having SEQ ID NO:1, to multiple copies of a peptide having SEQ ID NO:2, multiple copies of a toxin having SEQ ID NO: 3 and to multiple copies of a toxin having SEQ ID NO: 4. According to some embodiments, the present invention provides a construct comprising a PEG scaffold bound to multiple copies of a peptide of SEQ ID NO:1, to multiple copies of a peptide of SEQ ID NO:2, multiple copies of a toxin of SEQ ID NO: 3 and to multiple copies of a toxin of SEQ ID NO: 4. According to one embodiment, the molar ratio of the toxin having the amino acid SEQ ID NO: 3 to the toxin having the amino acid SEQ ID NO: 4 is about 0.1:1 to about 10:1 or 1:1. According to some embodiments, the stoichiometric molar ratio between the peptide having SEQ ID NO:1, the peptide of SEQ ID NO:2, the toxin having SEQ ID NO: 3 and the toxin having SEQ ID NO: 3 is 1:1:3:3. According to other embodiments, the stoichiometric molar ratio between the peptide having SEQ ID NO:1, the peptide of SEQ ID NO: 2, the toxin having SEQ ID NO: 3 and the toxin having SEQ ID NO: 4 is selected from 1:2:3:2, 1:2:2:3, 2:1:3:2, 2:1:2:3 and 2:2:2:2. In the abovementioned embodiments, the peptides comprising or consisting of SEQ ID NO: 1 or 2 are cyclopeptides and the toxins comprising or consisting of SEQ ID NO: 3 or 4 are cyclotoxins. According to some embodiments, the construct of the present invention has a synergistic cytotoxicity, therefore such pharmaceutical composition, when administered, provides a profound therapeutic effect.

According to any one of the above embodiments, the pharmaceutical composition comprises a plurality of the constructs according to the present invention and according to the above embodiments.

According to another embodiment, the present invention provides a pharmaceutical composition according to the present invention, for use in treating a cell proliferative disease or disorder. According to some embodiments, the cell proliferative disease or disorder is cancer. Thus, according to one embodiment, the pharmaceutical composition of the present invention is for use in treating cancer.

The terms "treating" of "treatment of" a condition or patient refers to taking steps to obtain beneficial or desired results, including clinical results. Beneficial or desired clinical results include, but are not limited to, or ameliorating abrogating, substantially inhibiting, slowing or reversing the progression of a disease, condition or disorder, substantially ameliorating or alleviating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and/or (e) limiting recurrence of symptoms in patients that were previously asymptomatic for the disorder(s).

According to some embodiments, treating cancer comprises preventing or treatment tumor metastasis. According to certain embodiments, the metastasis is decreased. According to other embodiments, the metastasis is prevented.

According to some embodiments, treating cancer comprises increasing the duration of survival of a subject having cancer, comprising administering to the subject in need thereof a composition comprising a construct defined above whereby the administration of the construct increases the duration of survival.

According to some embodiments, treating cancer comprises increasing the progression of free survival of a subject having cancer.

According to some embodiments, treating cancer comprises increasing the duration of response of a subject having cancer. According to other embodiments, treating cancer comprises preventing tumor recurrence.

The cancer amendable for treatment according to the present invention includes, but not limited to: carcinoma, lymphoma, blastoma, sarcoma, and leukemia or lymphoid malignancies. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high-grade immunoblastic NHL; high-grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

According to some embodiments, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers.

According to other embodiments, the cancer is a solid cancer.

The pharmaceutical composition according to the present invention may be administered as a stand-alone treatment or in combination with a treatment with any other agent. According to a specific embodiment, constructs according to the present invention are administered to a subject in need thereof as part of a treatment regimen in combination with at least one anti-cancerous agent. The pharmaceutical composition according to the present invention may be administered in combination with the anti-cancerous agent or separately.

The pharmaceutical composition according to the present invention may be administered together with an anti-neoplastic composition.

According to a specific embodiment, the anti-neoplastic composition comprises at least one chemotherapeutic agent.

The term "anti-neoplastic composition" refers to a composition useful in treating cancer comprising at least one active therapeutic agent capable of inhibiting or preventing tumor growth or function or metastasis, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1l (e.g., Agnew, Chem Intl. Ed. Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane;

folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2', 2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophorfree, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy DNA-based vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

According to another aspect, the present invention provides a method of treating cancer in a subject in need thereof comprising administering to said subject a pharmaceutical composition of the present invention. According to one embodiment, the present invention provides a method of treating cancer in a subject in need thereof comprising administering to said subject a therapeutically effective amount of a construct of the present invention. According to some embodiments, the pharmaceutical composition is administered as part of a treatment regimen together with at least one anti-cancer agent. The term "therapeutically effective amount" is an amount of a drug, compound, construct etc. that, when administered to a subject will have the intended therapeutic effect. The full therapeutic effect does not necessarily occur by administration of one dose, and may occur only after administration of a series of doses.

According to another aspect, the present invention provides a peptide that binds specifically to human eukaryotic Elongation Factor 2 (eEF2), an analog or fragment thereof. According to one embodiment, the present invention provides a peptide that binds specifically to human eEF2. According to some embodiments, the peptide is a toxin. According some embodiments, the peptide consists of 5 to 30 amino acids. According to other embodiments, each peptide consists of 6 to 25 amino acids. According to yet other embodiments, each peptide consists of 7 to 20 amino acids. According to some embodiments, each peptide consists of 8, 9, 10, 11, 12, 13, 14, 15, 16, 17, 18, 19 or 20 amino acids. Each possibility represents a separate embodiment of the invention.

According to some embodiments, the peptide that binds to human eEF2 is a peptide having SEQ ID NO: 3. According to certain embodiments the present invention provides an analog of SEQ ID NO:3. According to a further embodiment, the present invention provides a the fragment of the peptide or of the analog. According to one embodiment, the peptide is a peptide having SEQ ID NO: 3. According to another embodiment, the peptide is a peptide of SEQ ID NO: 3. According to some embodiments, the peptide is a cyclic peptide.

According to some embodiments, the analog has a sequence identity of at least 70%, at least 80%, or at least 90% to SEQ ID NO: 3. According to some embodiments, the analog has at least 70%, at least 75%, at least 80%, at least 85, at least 90% or at least 95% sequence identity to SEQ ID NO: 3. According to other embodiments, the analog has about 70% to 95%, 75% to 90%, or 80% to 85% sequence identity to SEQ ID NO: 3. According to some embodiments, the analog is a conservative analog of SEQ ID NO: 3. According to some embodiments, the conservative analog of SEQ ID NO: 3 has 1, 2, 3, 4 or 5 conservative substitutions in SEQ ID NO: 3. According to some embodiments, the analog is a cyclopeptide.

According to one embodiment, the fragment consists of 6 to 11, 7 to 10 or 8 to 9 consecutive amino acids of SEQ ID NO: 3 or analog thereof.

According to some embodiments, the peptide comprising or consisting of SEQ ID NO: 3 enhances the activity of human eEF2. According to one embodiment, the peptide is an agonist of eEF2. According to another embodiment, the analog of SEQ ID NO: 3 or the fragment of the peptide or the analog enhances the activity of eEF2.

According to one embodiment, the peptide comprising or consisting of SEQ ID NO:3, analog thereof or the fragment of the peptide or said analog is a toxin. In one embodiment, the peptide is for use in inducing cell death in target cells. According to some embodiments, the cells are cancer cells. According to one embodiment, the peptide comprising SEQ ID NO:3 is for use in inducing cell death in target cells. According to another embodiment, the peptide consisting of SEQ ID NO:3 is for use in inducing cell death in target cells. According to a further embodiment, the analog of a peptide comprising or consisting of SEQ ID NO: 3 is for use in inducing cell death in target cells.

The terms "induce cell death" and "promote cell death" are used herein interchangeably and mean that the of the present invention (i.e. the peptide, the analog or the fragment) can directly inducing cell death to cells, where cell death includes apoptosis and necrosis. The cell death may be caused due to interaction of the compound of the present invention with molecules molecule expressed on the cell surface or with molecules located within the cell such as molecule located in the cytosol, bound to the inner side of the cell membrane, located in the organelles or present on the membrane of the organelles, either inner or outer part of it.

The term "cell death" as used herein encompasses both destruction and damage or impairment of cells. The term "cell death" encompasses cell ablation.

According to some embodiments, the peptide that binds to human eEF2 is a peptide having SEQ ID NO: 4. According to certain embodiments, the present invention provides an analog of SEQ ID NO: 4. According to a further embodiment, the present invention provides a fragment of the peptide or of the analog. According to one embodiment, the peptide is a peptide having SEQ ID NO: 4. According to another embodiment, the peptide is a peptide of SEQ ID NO: 4. According to some embodiments, the peptide is a cyclic peptide.

According to some embodiments, the analog has a sequence identity of at least 70%, at least 80%, or at least 90% to SEQ ID NO: 4. According to some embodiments, the analog is a conservative analog of SEQ ID NO: 4. According to other embodiments, the analog has 70% to 95%, 75% to 90%, or 80% to 85% identity to SEQ ID NO: 4. According to some embodiments, the analog is a conservative analog of SEQ ID NO: 4. According to some embodiments, the conservative analog of SEQ ID NO: 4 has 1, 2, 3, 4 or 5 conservative substitutions in SEQ ID NO: 4. According to some embodiments, the analog is a cyclic peptide.

According to one embodiment, the fragment consists of 6 to 11, 7 to 10 or 8 to 9 consecutive amino acids of SEQ ID NO: 4 or analog thereof.

According to some embodiments, the peptide comprising or consisting of SEQ ID NO: 4 enhances the activity of human eEF2. According to one embodiment, the peptide is an agonist of eEF2. According to another embodiment, the analog of SEQ ID NO: 4 or the fragment of the peptide or the analog enhances the activity of eEF2.

According to one embodiment, the peptide comprising or consisting of SEQ ID NO: 4, analog thereof or the fragment of the peptide or said analog is a toxin. In one embodiment, the peptide is for use in inducing cell death in target cells. According to some embodiments, the cells are cancer cells. According to one embodiment, the peptide comprising SEQ ID NO: 4 is for use in inducing cell death in target cells. According to another embodiment, the peptide consisting of SEQ ID NO: 4 is for use in inducing cell death in target cells. According to a further embodiment, the analog of a peptide comprising or consisting of SEQ ID NO: 4 is for use in inducing cell death in target cells.

According to another aspect, the present invention provides a conjugate of the peptide that binds specifically to human eEF2.

According to one embodiment, the present invention provides a conjugate of the peptide selected from a peptide having or consisting of SEQ ID NO: 3, analog thereof or fragment thereof. According to one embodiment, the present invention provides a conjugate of the cyclopepide having or consisting of SEQ ID NO: 3.

According to one embodiment, the present invention provides a conjugate of the peptide selected from a peptide having or consisting of SEQ ID NO: 4, analog thereof or fragment thereof. According to one embodiment, the present invention provides a conjugate of the cyclopepide having or consisting of SEQ ID NO: 4.

The term "conjugate" refers to any substance formed from the joining together or binding of two or more molecules. In particular, the term conjugate encompasses a compound formed from binding of two or more peptides of any one of the above embodiments or a compound comprising said peptide bound to another molecule. According to some embodiments, the peptide, analog or fragment of the present invention is conjugated with a carrier protein or moiety which improves the peptide's antigenicity, solubility, stability or permeability. A fusion protein comprising at least one peptide according to the invention is also within this scope.

Thus, according to some embodiments, the conjugate comprises at least two copies of the peptides comprising or consisting of SEQ ID NO: 3, analog or fragment thereof covalently bound.

According to another embodiment, the conjugate comprises at least one peptide comprising or consisting of SEQ ID NO: 3, analog or fragment thereof and another molecule. According to some embodiments, said molecule can be any molecule. According to one embodiment, the molecule is selected from an active agent, an extracellular tumor antigen targeting molecule, a carrier, a toxin, a permeability-enhancing moiety and an anti-cancer agent.

According to some embodiments, the conjugate comprises at least two copies of the peptide comprising or consisting of SEQ ID NO: 4, analog or fragment thereof covalently bound.

According to another embodiment, the conjugate comprises at least one peptide comprising or consisting of SEQ ID NO: 4, analog or fragment thereof and another molecule. According to some embodiments, said molecule can be any molecule. According to one embodiment, the molecule is selected from an active agent, an extracellular tumor antigen targeting molecule, a carrier, a toxin, a permeability-enhancing moiety and an anti-cancer agent.

The extracellular tumor antigen targeting molecule, a carrier, a toxin, an anti-cancer agent are as defined according to the present invention. The term "active agent" refers to an agent that has biological activity, pharmacologic effects and/or therapeutic utility.

According to one embodiment, the extracellular tumor antigen is selected from EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR.

According to another embodiment, the toxin is selected from the group consisting of a toxin binding to a eukaryotic elongation factor 2, BIM-BH3 toxin having the amino acid sequence set forth in SEQ ID NO: 5, Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, and cyanotoxin.

According to yet another embodiment, the carrier may be a scaffold carrier such as PEG carrier or peptidic carrier.

According to some embodiments, the conjugate of the present invention is for use in inducing cell death in target cells.

According to another aspect, the present invention provides a peptide comprising the amino acids sequence set forth in SEQ ID NO: 1. According to one embodiment, the present invention provides an analog of the peptide having SEQ ID NO:1. According to a further embodiment, the present invention provides a fragment of said peptide or said analog. According to one embodiment, the peptide consists of SEQ ID NO: 1.

According to some embodiments, the peptide consists of 5 to 30 amino acids. According to other embodiments, each peptide consists of 6 to 25 amino acids. According to yet other embodiments, each peptide consists of 7 to 20 amino acids. According to some embodiments, each peptide consists of 8, 9, 10, 11, 12, 13, 14, 15, 16, 17, 18, 19 or 20 amino acids. Each possibility represents a separate embodiment of the invention.

According to some embodiments, the peptide having or consisting of SEQ ID NO:1, the analog or the fragment thereof binds specifically to a human Epidermal Growth Factor Receptor (EGFR). According to one embodiment, the peptide, analog of the fragment is an antagonist of EGFR. According to some embodiments, the peptide is a cyclopeptide.

According to some embodiments, the analog of SEQ ID NO: 1 has a sequence identity of at least 70%, at least 80%, or at least 90% to SEQ ID NO: 1. According to other embodiments, the analog has 70% to 95%, 75% to 90%, or 80% to 85% sequence identity to SEQ ID NO: 1. According to some embodiments, the analog is a conservative analog of SEQ ID NO: 1. According to some embodiments, the conservative analog of SEQ ID NO: 1 has 1, 2, 3, 4 or 5 conservative substitutions. According to some embodiments, the analog is a cyclopeptide.

According to one embodiment, the fragment consists of 6 to 11, 7 to 10 or 8 to 9 consecutive amino acids of SEQ ID NO: 1 or of analog thereof.

According to some embodiments, the peptide comprising or consisting of SEQ ID NO:1, analog or fragment thereof is a cancer cells targeting peptide. Thus, in one embodiment, the peptide comprising or consisting of SEQ ID NO:1, analog or fragment thereof is for use in cancer cell targeting.

According to one embodiment, the present invention provides a conjugate of the peptide selected from a peptide having or consisting of SEQ ID NO: 1, analog thereof or fragment thereof. According to one embodiment, the present invention provides a conjugate of the cyclopepide having or consisting of SEQ ID NO: 1.

According to some embodiments, the conjugate comprises at least two copies of the peptide comprising or consisting of SEQ ID NO: 1, analog or fragment thereof covalently bound. According to another embodiment, the conjugate comprises at least one peptide comprising or consisting of SEQ ID NO: 1, analog or fragment thereof and another molecule. According to some embodiments, said molecule can be any molecule. According to one embodiment, the molecule is selected from an active agent, an extracellular tumor antigen targeting molecule, a carrier, a permeability-enhancing moiety, a toxin, an anti-cancer agent and a combination thereof.

The terms extracellular tumor antigen targeting molecule, a carrier, a toxin, an anti-cancer agent are as defined in the present invention.

According to one embodiment, the extracellular tumor antigen is selected from EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR.

According to another embodiment, the toxin is selected from the group consisting of a toxin binding to a eukaryotic elongation factor 2, BIM-BH3 toxin of SEQ ID NO: 5, Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, and cyanotoxin.

According to yet another embodiment, the carrier may be a scaffold carrier such as PEG carrier or peptidic carrier.

According to another aspect, the present invention provides a peptide comprising the amino acids sequence set forth in SEQ ID NO: 2. According to one embodiment, the present invention provides an analog of the peptide having SEQ ID NO:2. According to a further embodiment, the present invention provides a fragment of said peptide or said analog. According to one embodiment, the peptide consists of SEQ ID NO: 2.

According some embodiments, the peptide consists of 5 to 30 amino acids. According to other embodiments, each peptide consists of 6 to 25 amino acids. According to yet other embodiments, each peptide consists of 7 to 20 amino acids. According to some embodiments, each peptide consists of 8, 9, 10, 11, 12, 13, 14, 15, 16, 17, 18, 19 or 20 amino acids. Each possibility represents a separate embodiment of the invention.

According to some embodiments, the peptide having or consisting of SEQ ID NO:2, the analog or the fragment thereof binds specifically to a human Programmed death-ligand 1 (PD-L1).

According to any one of the above embodiments, the peptide, analog of the fragment is an antagonist of PD-L1.

According to some embodiments, the peptide is a cyclopeptide.

According to some embodiments, the analog of SEQ ID NO: 2 has a sequence identity of at least 70%, at least 80%, or at least 90% to SEQ ID NO: 2. According to other embodiments, the analog has 70% to 95%, 75% to 90%, or 80% to 85% identity to SEQ ID NO: 2. According to some embodiments, the analog is a conservative analog of SEQ ID NO: 2. According to some embodiments, the conservative analog of SEQ ID NO: 2 has 1, 2, 3, 4 or 5 conservative substitutions. According to some embodiments, the analog is a cyclopeptide.

According to one embodiment, the fragment consists of 6 to 11, 7 to 10 or 8 to 9 consecutive amino acids of SEQ ID NO: 2 or of an analog thereof.

According to some embodiments, the peptide comprising or consisting of SEQ ID NO:2, analog or fragment thereof is a cancer cells targeting peptide. Thus, in one embodiment, the peptide comprising or consisting of SEQ ID NO:2, analog or fragment thereof is for use in cancer cell targeting.

According to one embodiment, the present invention provides a conjugate of the peptide selected from a peptide having or consisting of SEQ ID NO: 2, analog thereof or fragment thereof. According to one embodiment, the present invention provides a conjugate of the cyclopepide having or consisting of SEQ ID NO: 2.

Thus, according to some embodiments, the conjugate comprises at least two copies of the peptide comprising or consisting of SEQ ID NO: 2, analog or fragment thereof covalently bound. According to another embodiment, the conjugate comprises at least one peptide comprising or consisting of SEQ ID NO: 2, analog or fragment thereof and another molecule. According to some embodiments, said molecule can be any molecule. According to one embodiment, the molecule is selected from an active agent, an extracellular tumor antigen targeting molecule, a carrier, a toxin, an anti-cancer agent, a permeability-enhancing moiety and a combination thereof.

The extracellular tumor antigen targeting molecule, a carrier, a toxin, an anti-cancer agent are as defined in the present invention.

According to one embodiment, the extracellular tumor antigen is selected from EGFR, PD-L1, HER2, androgen receptor, benzodiazepine receptor, Cadherin, CXCR4, CTLA-4, CD2, CD19, endothelin receptor, ERBB4, FGFR, folate receptor, HER4, HGFR, Mucin 1, OGFR, PD-1, PD-L2, PDGFR, and VEGFR.

According to another embodiment, the toxin is selected from the group consisting of a toxin binding to a eukaryotic elongation factor 2, BIM-BH3 toxin having the amino acid sequence set forth in SEQ ID NO: 5, Diphtheria toxin, *Pseudomonas* exotoxin, Anthrax toxin, botulinum toxin, Ricin, PAP, Saporin, Gelonin, Momordin, ProTx-I ProTx-II, *Conus californicus* toxin, snake-venom toxin, cyanotoxin, and any combination thereof.

According to yet another embodiment, the carrier may be a scaffold carrier such as PEG carrier of peptidic carrier.

According to another aspect, the present invention provides a composition comprising the peptide of the present invention, or the conjugate of the present invention. According to one embodiment, the composition is a pharmaceutical composition. Thus, in some embodiments, the present invention provides a pharmaceutical composition comprising the peptide of the present invention, or the conjugate of the present invention.

According to one embodiment, the pharmaceutical composition comprises a peptide comprising or consisting of SEQ ID NO: 1 according to any one of the above embodiments. According to another embodiment, the pharmaceutical composition comprises the analog of SEQ ID NO: 1 or a fragment of said peptide or said analog. According to some embodiments, the pharmaceutical composition comprises a plurality of said peptides, analogs or fragments. According to yet another embodiment, the pharmaceutical composition comprises one or more conjugates of the peptide comprising or consisting of SEQ ID NO:1, analog or fragment thereof according to any one of the above embodiments.

According to some embodiments, the pharmaceutical composition comprises a peptide comprising or consisting of SEQ ID NO: 2 according to any one of the above embodiments. According to another embodiment, the pharmaceutical composition comprises the analog of SEQ ID NO: 2 or a fragment of said peptide or said analog.

According to some embodiments, the pharmaceutical composition comprises a plurality of said peptides, analogs or fragments. According to yet another embodiment, the pharmaceutical composition comprises one or more conjugates of the peptide comprising or consisting of SEQ ID NO:2, analog or fragment thereof according to any one of the above embodiments.

According to certain embodiments, the pharmaceutical composition comprises a peptide comprising or consisting of SEQ ID NO: 3 according to any one of the above embodiments. According to another embodiment, the pharmaceutical composition comprises the analog of SEQ ID NO: 3 or a fragment of said peptide or said analog. According to some embodiments, the pharmaceutical composition comprises a plurality of said peptides, analogs or fragments. According to yet another embodiment, the pharmaceutical composition comprises one or more conjugates of the peptide comprising or consisting of SEQ ID NO:3, analog or fragment thereof according to any one of the above embodiments.

According to another embodiment, the pharmaceutical composition comprises a peptide comprising or consisting of SEQ ID NO: 4 according to any one of the above embodiments. According to another embodiment, the pharmaceutical composition comprises the analog of SEQ ID NO: 4 or a fragment of said peptide or said analog. According to some embodiments, the pharmaceutical composition comprises a plurality of said peptides, analogs or fragments. According to yet another embodiment, the pharmaceutical composition comprises one or more conjugates of the peptide comprising or consisting of SEQ ID NO:4, analog or fragment thereof according to any one of the above embodiments.

All definitions and embodiments of other aspects of the present invention related to said peptides and conjugates are encompassed by this aspect as well.

According to some embodiments, the pharmaceutical composition is for treating a cell proliferative disease or disorder. According to some embodiments, cell proliferative disease or disorder is cancer. According to one embodiment, the pharmaceutical composition comprises a peptide selected from a peptide comprising or consisting of amino acid sequence selected from SEQ ID NO: 1, 2, 3 and 4, analog thereof or fragment thereof, as defined in any one of the embodiments of the present invention. Thus, in certain embodiment, the present invention provides a pharmaceutical composition comprising a peptide comprising or consisting of SEQ ID NO: 1 for use in treating cancer. According to a further embodiment, the present invention provides a pharmaceutical composition comprising a peptide comprising or consisting of SEQ ID NO: 2 for use in treating cancer. According to yet another embodiment, the present invention provides a pharmaceutical composition comprising a peptide comprising or consisting of SEQ ID NO: 3 for use in treating cancer. According to certain embodiments, the present invention provides a pharmaceutical composition comprising a peptide comprising or consisting of SEQ ID NO: 4 for use in treating cancer. According to another embodiment, the pharmaceutical composition comprises one or more conjugates of said peptides as defined in any one of the embodiments of the present invention.

According to another aspect, the present invention provides a method of treating a proliferative disease or disorder in a subject in need thereof comprising administering a therapeutically effective amount of the peptides or conjugates of the present invention. According to one embodiment, the method comprises administering a pharmaceutical composition comprising the peptides or conjugates of the present invention. According to one embodiments, the peptide is selected from the group consisting of a peptide comprising or consisting of SEQ ID NO: 1, a peptide comprising or consisting of SEQ ID NO: 2, a peptide comprising or consisting of SEQ ID NO: 3, a peptide comprising or consisting of SEQ ID NO: 4, analogs thereof, and fragments of said peptides. According to one embodiment, the conjugate is a conjugated of said peptides. According to one embodiment, the peptide, analog or fragment is cyclic.

According to another aspect, the present invention provides an isolated polynucleotide comprising a sequence encoding the peptide selected from a peptide comprising or consisting of amino acid sequence selected from SEQ ID NO: 1, 2, 3 and 4. According to some embodiment, the polynucleotide comprises a sequence encoding an analog of a peptide selected from a peptide comprising or consisting of amino acid sequence selected from SEQ ID NO: 1, 2, 3 and 4, or fragment thereof, as defined in any one of the embodiments of the present invention.

According to some embodiments, the polynucleotide comprises a sequence encoding the peptide comprising or consisting of SEQ ID NO: 1, analog thereof or fragment thereof. According to one embodiment, the polynucleotide comprises the sequence encoding the peptide having SEQ ID NO: 1. According to another embodiment, the polynucleotide comprises the sequence encoding the peptide of SEQ ID NO: 1.

According to certain embodiments, the polynucleotide comprises a sequence encoding the peptide comprising or consisting of SEQ ID NO: 2, analog thereof or fragment thereof. According to one embodiment, the polynucleotide comprises the sequence encoding the peptide having SEQ ID NO: 2. According to another embodiment, the polynucleotide comprises the sequence encoding the peptide of SEQ ID NO: 2.

According to another embodiment, the polynucleotide comprises a sequence encoding the peptide comprising or consisting of SEQ ID NO: 3, analog thereof or fragment thereof. According to one embodiment, the polynucleotide comprises the sequence encoding the peptide having SEQ ID NO: 3. According to another embodiment, the polynucleotide comprises the sequence encoding the peptide of SEQ ID NO: 3.

According to yet another embodiment, the polynucleotide comprises a sequence encoding the peptide comprising or consisting of SEQ ID NO: 4, analog thereof or fragment thereof. According to one embodiment, the polynucleotide comprises the sequence encoding the peptide having SEQ ID NO: 4. According to another embodiment, the polynucleotide comprises the sequence encoding the peptide of SEQ ID NO: 4

According to one embodiment, the present invention provides a polynucleotide comprising a sequence encoding a polypeptide comprising at least one copy of (i) SEQ ID NO: 1, (ii) SEQ ID NO: 2 and (iii) SEQ ID NO: 3. According to another embodiment, the polynucleotide comprises a sequence encoding a polypeptide comprising at least one copy of (i) SEQ ID NO: 1, (ii) SEQ ID NO: 2 and (iii) SEQ ID NO: 4. According to a further embodiment, the polynucleotide comprises a sequence encoding a polypeptide comprising at least one copy of (i) SEQ ID NO: 1, (ii) SEQ ID NO: 2, (iii) SEQ ID NO: 3 and SEQ ID NO: 4.

According to another aspect, the present invention provides a nucleic acid construct, comprising the polynucleotide according to any one of the above embodiments. According to one embodiment, the polynucleotide is operably linked to a promoter. According to one embodiment, the nucleic acid construct comprises a polynucleotide comprising a sequence encoding the peptide selected from a peptide comprising or consisting of amino acid sequence selected from SEQ ID NO: 1, 2, 3 and 4, analog thereof or fragment thereof, as defined in any one of the embodiments of the present invention. According to another embodiment, the nucleic acid construct comprises a polynucleotide comprising a sequence encoding the comprising a sequence encoding a polypeptide comprising at least one copy of (i) SEQ ID NO: 1, (ii) SEQ ID NO: 2 and (iii) SEQ ID NO: 3. According to another embodiment, the polynucleotide comprises a sequence encoding a polypeptide comprising at least one copy of (i) SEQ ID NO: 1, (ii) SEQ ID NO: 2 and (iii) SEQ ID NO: 4. According to a further embodiment, the polynucleotide comprises a sequence encoding a polypeptide comprising at least one copy of (i) SEQ ID NO: 1, (ii) SEQ ID NO: 2, (iii) SEQ ID NO: 3 and SEQ ID NO: 4.

The term "nucleic acid construct", as used herein, refers to an artificially constructed segment of nucleic acid. It can be an isolated or integrated in another nucleic acid molecule.

As used herein, the term "operably linked", "operably encodes", and "operably associated" are used herein interchangeably and refer to the functional linkage between a promoter and nucleic acid sequence, wherein the promoter initiates transcription of RNA corresponding to the DNA sequence.

The term "promoter" is a regulatory sequence that initiates transcription of a downstream nucleic acid. The term "promoter" refers to a DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible. A constitutive promoter is a promoter that is active under most environmental and developmental conditions. An inducible promoter is a promoter that is active under environmental or developmental regulation, e.g., upregulation in response to xylose availability.

According to another aspect, the present invention provides a vector comprising the polynucleotide sequence or the nucleic acid construct of the present invention. Thus, in one embodiment, the present invention provides a vector comprising the polynucleotide comprising a sequence encoding the peptide selected from a peptide comprising or consisting of amino acid sequence selected from SEQ ID NO: 1, 2, 3 and 4, analog thereof or fragment thereof, as defined in any one of the embodiments of the present invention. According to another embodiment, the vector comprises the polynucleotide comprising a sequence encoding a polypeptide comprising at least one copy of (i) SEQ ID NO: 1, (ii) SEQ ID NO: 2 and (iii) SEQ ID NO: 3. According to another embodiment, the polynucleotide comprises a sequence encoding a polypeptide comprising at least one copy of (i) SEQ ID NO: 1, (ii) SEQ ID NO: 2 and (iii) SEQ ID NO: 4. According to a further embodiment, the polynucleotide comprises a sequence encoding a polypeptide comprising at least one copy of (i) SEQ ID NO: 1, (ii) SEQ ID NO: 2, (iii) SEQ ID NO: 3 and SEQ ID NO: 4.

The terms "vector" and "expression vector" are used herein interchangeably and refer to any non-viral vector such as plasmid, cosmid, artificial chromosome (bacterial or yeast), or viral vector such as virus, retrovirus, bacteriophage, or phage, binary vector in double or single stranded linear or circular form, or nucleic acid, sequence which is able to transform host cells and optionally capable of replicating in a host cell. The vector may contain an optional marker suitable for use in the identification of transformed cells, e.g., tetracycline resistance or ampicillin resistance. According to one embodiment, the vector is a plasmid. According to another embodiment, the vector is a phage or bacteriophage.

The term "plasmid" refers to circular, optionally double-stranded DNA capable of inserting a foreign DNA fragment to a cell and optionally capable of autonomous replication in a given cell. Plasmids usually contain further sequences in addition to the ones, which should be expressed, like marker genes for their specific selection and in some cases sequences for their episomal replication in a target cell. In certain embodiments, the plasmid is designed for amplification and expression in bacteria. Plasmids can be engineered by standard molecular biology techniques.

According to another aspect, the present invention provides a cell comprising the polynucleotide comprising a sequence encoding the peptide selected from a peptide comprising or consisting of amino acid sequence selected from SEQ ID NO: 1, 2, 3 and 4, analog thereof or fragment thereof, as defined in any one of the embodiments of the present invention, the nucleic acid construct of the present invention. According to another embodiment, the present invention provides a cell comprising the polynucleotide comprising a sequence encoding the polypeptide comprising at least one copy of (i) SEQ ID NO: 1, (ii) SEQ ID NO: 2 and (iii) SEQ ID NO: 3. According to another embodiment, the polynucleotide comprises a sequence encoding a polypeptide comprising at least one copy of (i) SEQ ID NO: 1, (ii) SEQ ID NO: 2 and (iii) SEQ ID NO: 4. According to a further embodiment, the polynucleotide comprises a sequence encoding a polypeptide comprising at least one copy of (i) SEQ ID NO: 1, (ii) SEQ ID NO: 2, (iii) SEQ ID NO: 3 and SEQ ID NO: 4.

The terms "comprising", "comprise(s)" "include(s)," "having," "has," "contain(s)," as used in this specification means "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" may also encompass the meaning of "consisting" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

As used herein, the term "about", when referring to a measurable value such as an amount, a temporal duration, and the like, is meant to encompass variations of +/−10%, or +/−5%, +/−1%, or even +/−0.1% from the specified value.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Example 1. Library of Constructs

A library of constructs comprising a branched PEG, a toxin peptide and two target-binding peptides. Each construct comprises a branched PEG with eight connecting arms, each having an NHS (N-Hydroxysuccinimide) terminus to which an amino moiety of a peptide is connected. To each scaffold eight peptides are connected: six copies of a peptide toxin and 1 copy of each of two target-binding peptides.

Different combinations of peptide toxins and target-binding peptides are included in the different constructs of the library (see Table 1).

TABLE 1

Examples of constructs

| Construct No. | Toxin | Target-binding Peptides | |
|---|---|---|---|
| AE-1AB | Toxin 1 | Peptide A | Peptide B |
| AE-1AC | Toxin 1 | Peptide A | Peptide C |
| AE-1BC | Toxin 1 | Peptide B | Peptide C |
| AE-2AB | Toxin 2 | Peptide A | Peptide B |
| AE-2AC | Toxin 2 | Peptide A | Peptide C |
| AE-2BC | Toxin 2 | Peptide B | Peptide C |
| AE-3AB | Toxin 3 | Peptide A | Peptide B |
| AE-3BC | Toxin 3 | Peptide A | Peptide C |
| AE-3AC | Toxin 3 | Peptide B | Peptide C |

One exemplary arrangement is as following the toxins are 1—Nodularin, 2—ProTx-I, 3—Viperistatin fragment and the binding peptides are directed against the following targets: A—androgen receptor, B—ERBB4, and C—CXCR4.

Another exemplary arrangement is Toxin 1—cyclotoxin of SEQ ID NO: 3, Toxin 2—cyclo-toxin of SEQ ID NO: 4; Toxin 3—combination of cyclotoxins of SEQ ID NO: 3 and 4; the peptides are Peptide A—cyclic peptide SEQ ID NO: 1; Peptide B—cyclic peptide SEQ ID NO: 3; Peptide C is directed to bind androgen receptor, B—ERBB4, or C—CXCR4.

The constructs are synthesized using methods known in the art, including Fmoc-solid phase peptide synthesis, purified using HPLC and tested in in-vitro and in-vivo for a specific activity, such as anti-proliferative activity using assays and animal models well known in the art.

Example 2. Preparation of Cyclotoxins Tox1 and Tox2

Using the technique described in WO 2007/010525, cyclopeptides (referred as toxins or cyclotoxins Tox1 and Tox2) binding to human eukaryotic elongation factor 2 (eEF2) were generated and tested. The sequences of the cyclic peptides denoted as Tox1 (consisting of SEQ ID NO: 3) and Tox2 (consisting of SEQ ID NO: 4) are provided in Table 2.

TABLE 2

Two toxic peptides.

| | |
|---|---|
| Tox1 (SEQ ID NO: 3) | Cys-Ser-Ala-Arg-Trp-Gly-Pro-Thr-Met-Pro-Trp-Cys (S-S cyclic) |
| Tox2 (SEQ ID NO: 4) | Cys-Arg-Arg-Gly-Ser-Arg-Ala-Ser-Gly-Ala-His-Cys (S-S cyclic) |

Example 3. Binding of Tox1 and Tox2 to eEF2

Binding of Tox 1 and Tox2 to eEF2 was tested by ELISA using eEF2 or BSA as ligands.

Experimental Part 0.25 µg of target proteins, eEF2 (Human; Yeast derived) or BSA (negative control) were applied to several wells of maxisorp plate (NUNC) in 50 µl PBS and incubated overnight at 4° C. The solutions were removed, and each well was supplemented with 280 µl blocking solution (BSA 2 mg/ml). The plate was incubated 1 hr at 25° C.

To 1.5 ml tubes 100 µl of blocking solution+$10^9$ pfu (plaque forming units) of M13 phages that express the following peptides: eEF2-binding: RB, LBR1, TB2 (Tox2), YO2, GW (Tox1), DRB, PY, BW were added. The plate was incubated 1 hr at 25° C. The solution were discarded and the wells were washed 7 times with 280 μl washing solution (Tween 20 0.05%).

Each well was supplemented with 50 μl of HRP/Anti-M13 Monoclonal Conjugate (GE Healthcare) diluted 1:5000. The plate was incubated 1 hr at 25° C. The solutions were discarded and the wells were washed 7 times with 280 μl washing solution (Tween 20 0.05%). Each well was supplemented with 50 μl of TMB (T0440; Sigma).

Figure 2:
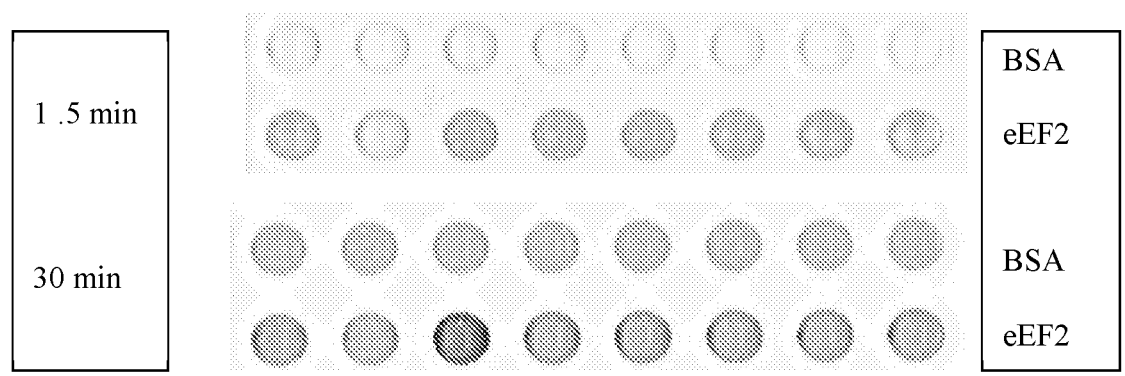
FIG. 2 shows the result of the ELISA experiment demonstrating the binding of several peptides (toxins) to eEF2 or BSA at two different incubation times: 1.5 min and 30 min (TB2—Tox2, GW ~Tox1).

The plate was photographed using a scanner after incubation time of 1.5 min and 30 min. It can be seen from FIG. 2 that Tox2 (denoted as TB2 in the figures) had the strongest effect.

Example 4. Tox1 and Tox2 Activate eEF2

The effect of Tox1 and Tox2 was tested in the in vitro transcription/translation system using HeLa Lysate system 1-Step Human Coupled IVT Kit-DNA (ThermoFisher Scientific). The following peptides were tested: GW (Tox1), DRB RB,TB2 (Tox2), and BW. In addition, a non eEF2-binding control peptide, GR, was also tested.

The IVT Kit components were mixed, and one portion was taken out to serve as a negative control. The rest of the mix was supplemented with pCFE-GFP DNA. This DNA, when transcribed and translated gives a fluorescence protein, GFP. The extent of fluorescence gives a measure of the extent of protein synthesis.

The mix was split into 9 ml aliquots. Each aliquot was supplemented with 1 ml of one concentration of a specific peptide. A positive control was supplemented with 1 ml of PBS. The reaction mixtures were incubated 4 hr at 30° C.

40 ml of PBS were added to each reaction mixtures. The mixtures were transferred to a 96 well black ELISA plate, and the fluorescence was measured at ex/em 482/512 nm.

Figure 3:
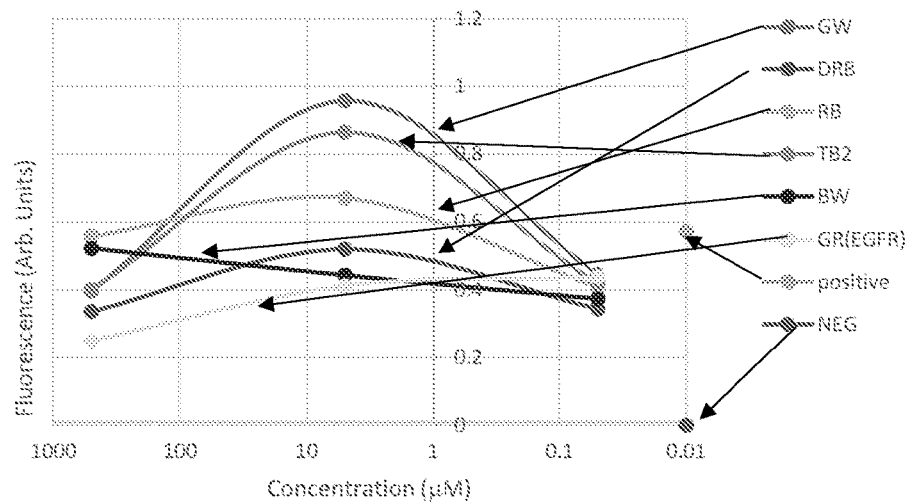
FIG. 3 shows the results of the activity of several peptides (toxins) tested in the in vitro transcription/translation system (TB2—Tox2, GW ~Tox1, GR—non-eEF2-binding control).
Figure 4A:
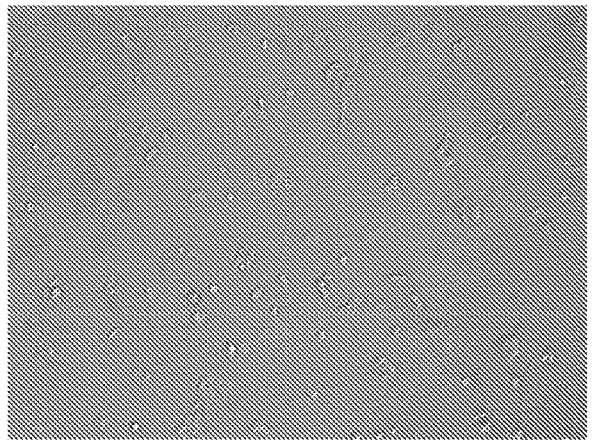
FIGS. 4A and 4B: A431 cell at T=0 and 48 h, respectively.
Figure 4C:
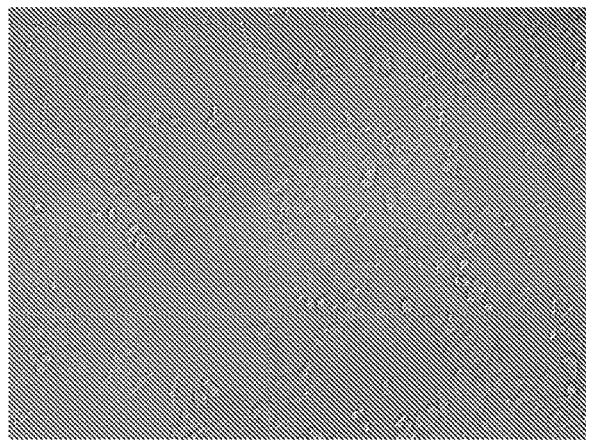
FIGS. 4C and 4D: MCS-7 cell at T=0 and 48 h, respectively.
Figure 4B:
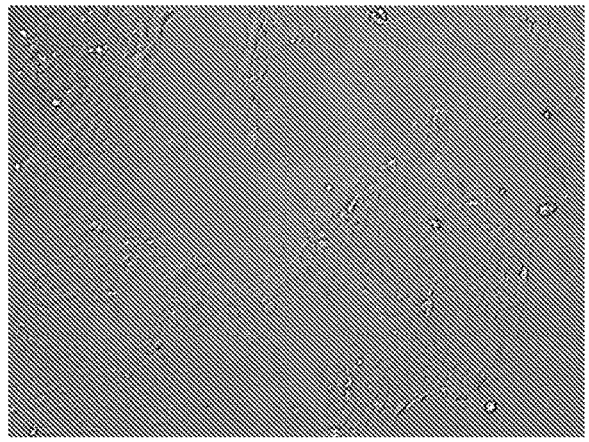
Figure 4D:
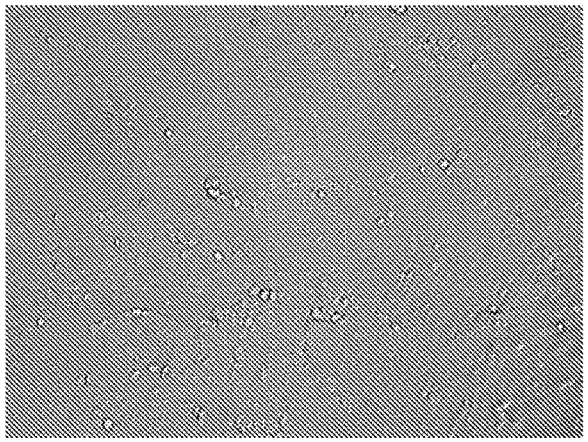
Figure 5A:
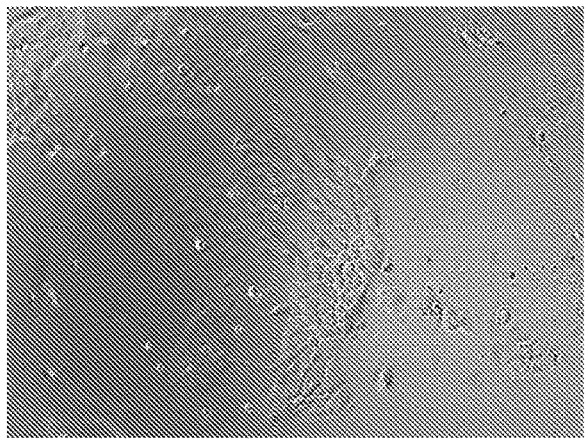
Figure 5D:
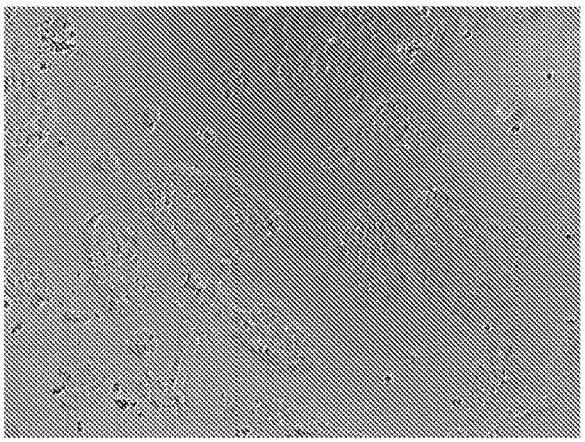
Figure 5B:
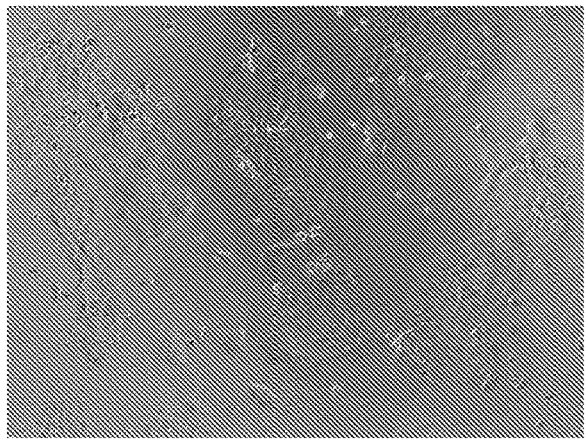
Figure 5E:
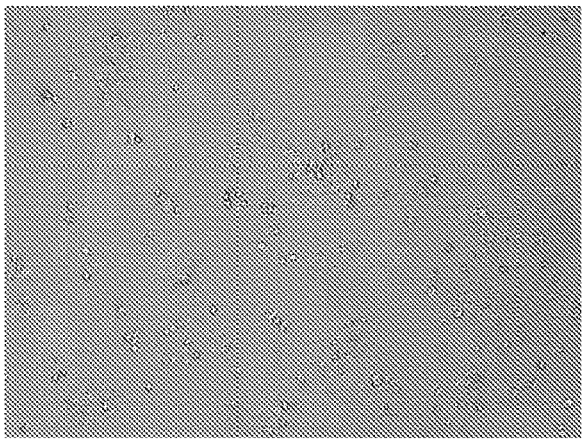
Figure 5C:
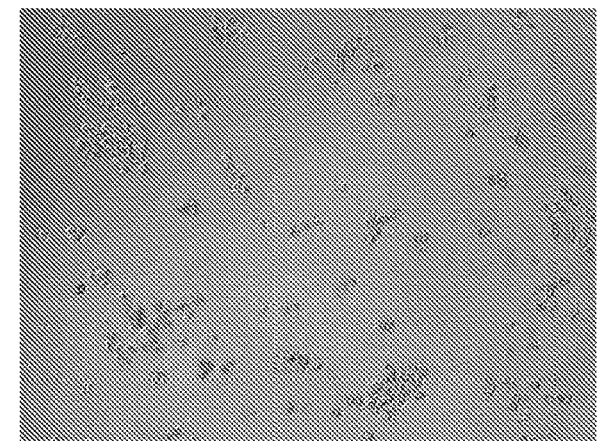
Figure 5F:
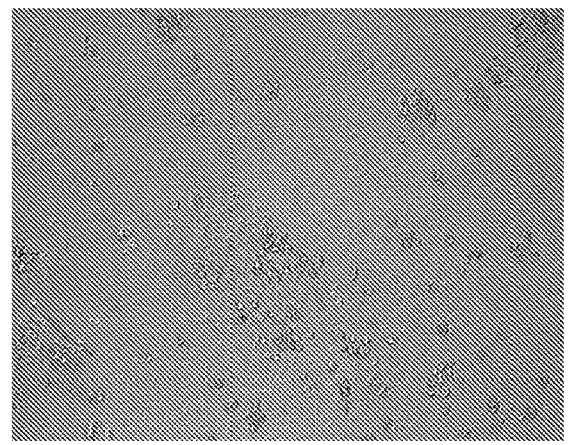
Figure 6A:
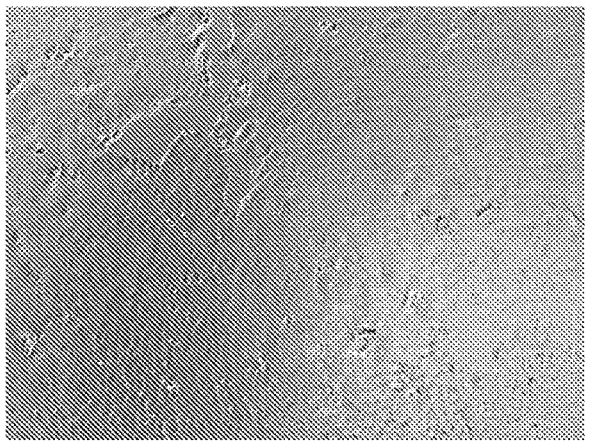
Figure 6D:
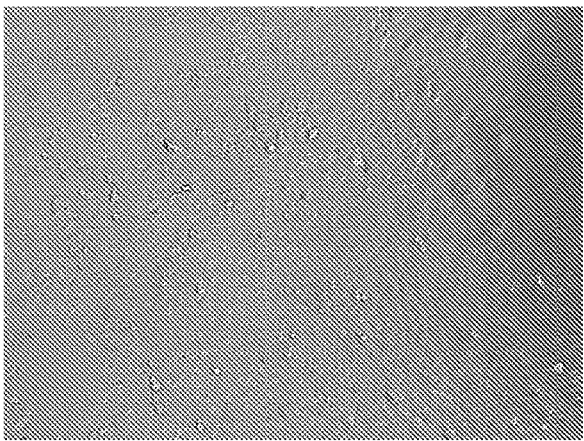
Figure 6B:
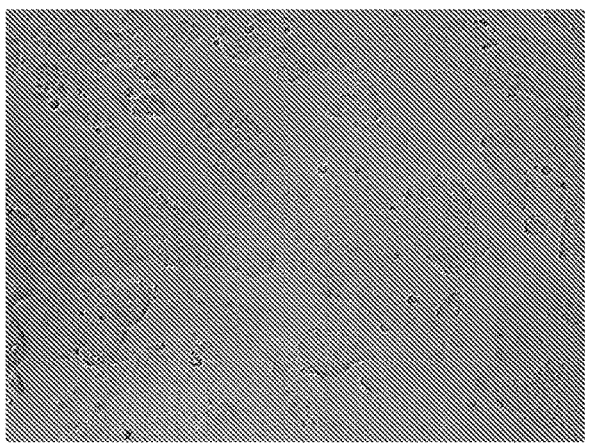
Figure 6E:
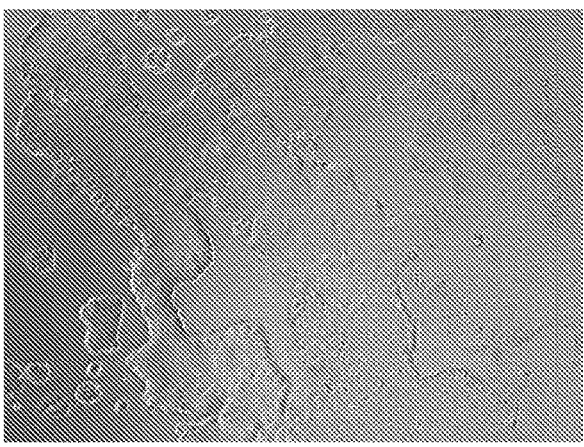
Figure 6C:
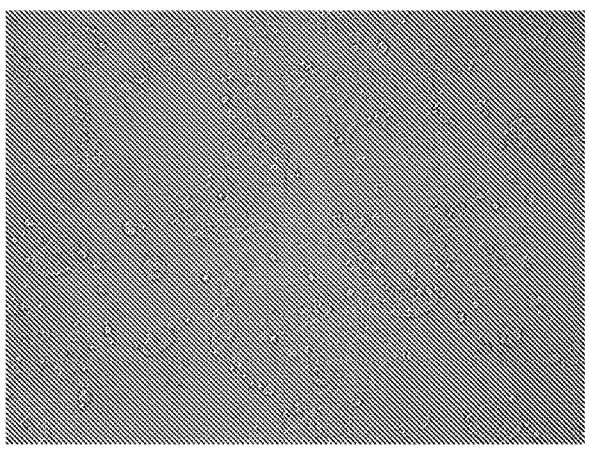
Figure 6F:
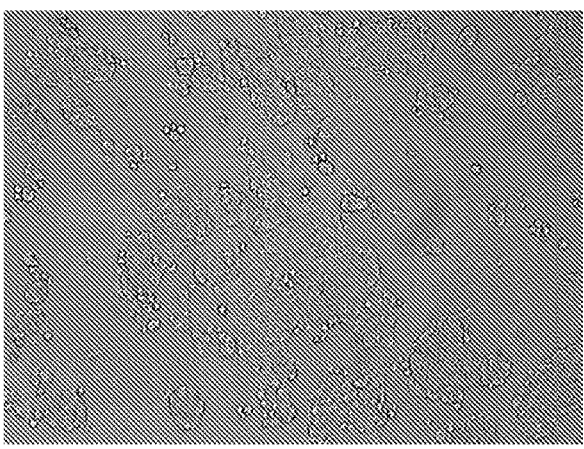
Figure 7A:
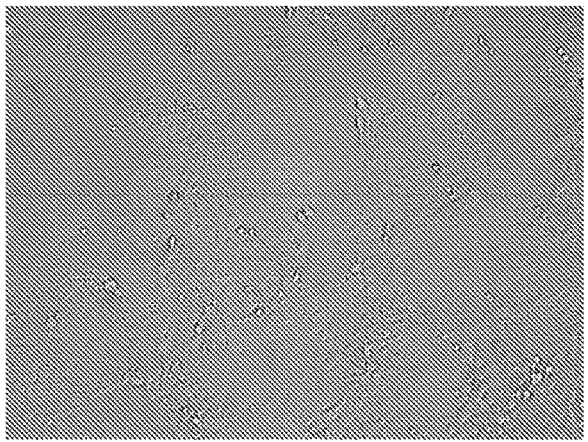
Figure 7D:
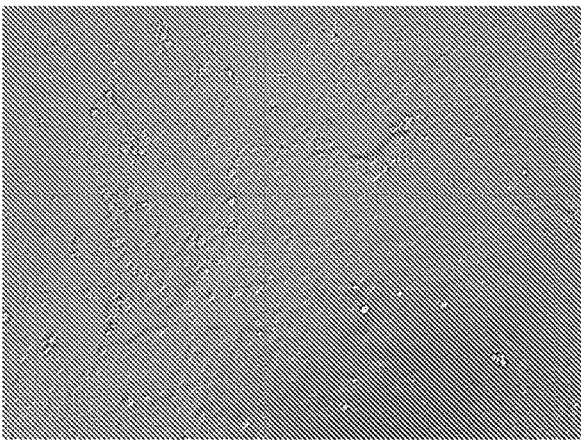
Figure 7B:
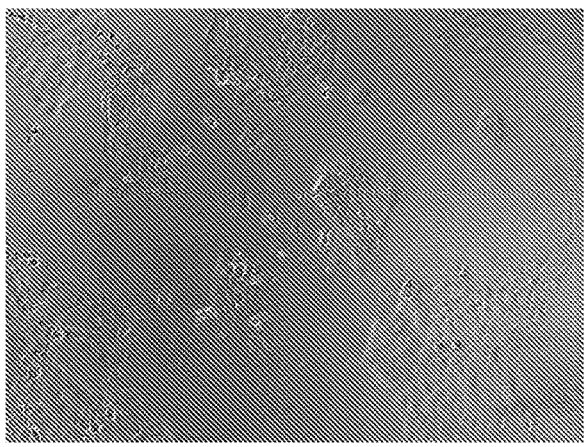
Figure 7E:
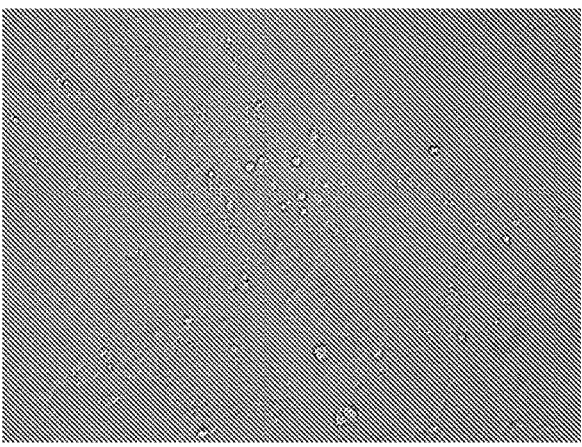
Figure 7C:
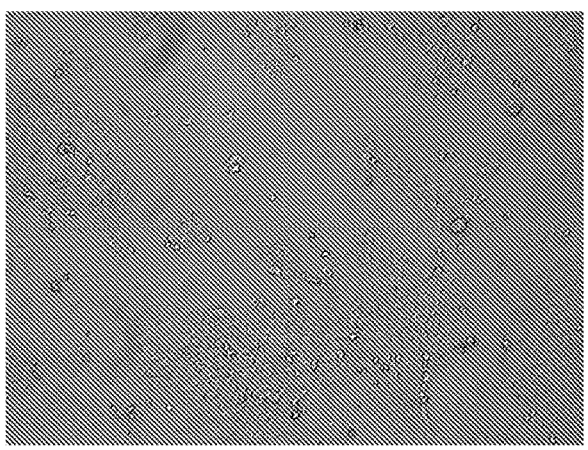
Figure 7F:
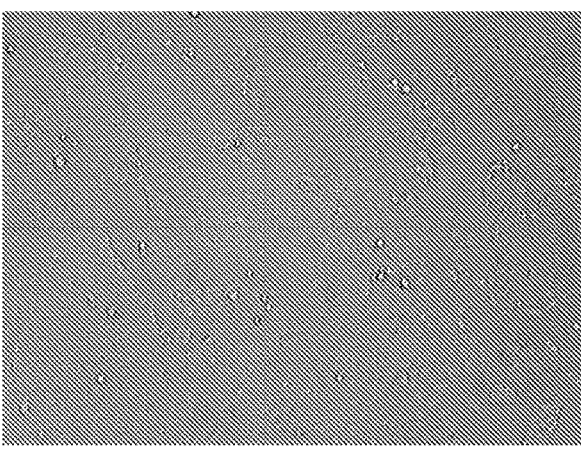
Figure 8A:
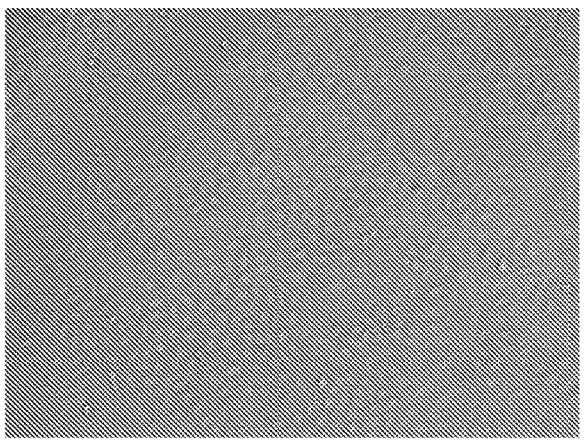
FIG. 8A is a control. The pictures were taken 48 hours after the treatment.
Figure 8B:
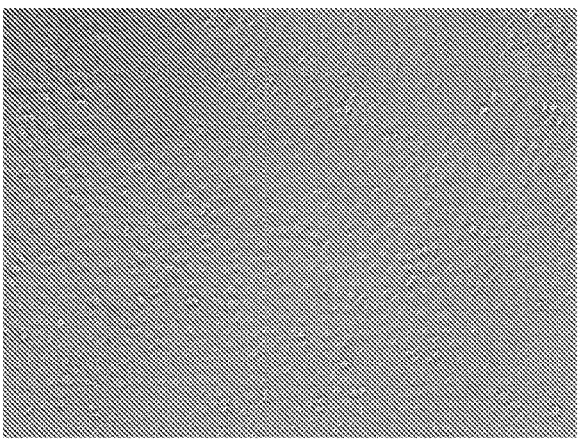
FIG. 8 shows the effect of treatment of A431 cells with different constructs: PEG-BIM (FIG. 8B-D), PEG-E13.3-BIM (FIG. 8E-G), PEG-PD-L1-GR-BIM (FIG. 8H-J) and PEG-PD-L1 GR-E13.3-BIM (FIG. 8K-M) at different concentrations: 10 nM (FIGS. 8B, 8E, 8H and 8K), 100 nM (FIGS. 8C, 8F, 8I and 8L) and 1 µM (FIGS. 8D, 8G, 8J and 8M).
Figure 8C:
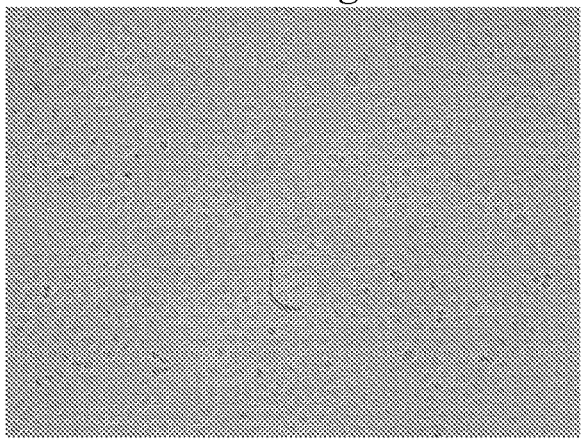
Figure 8D:
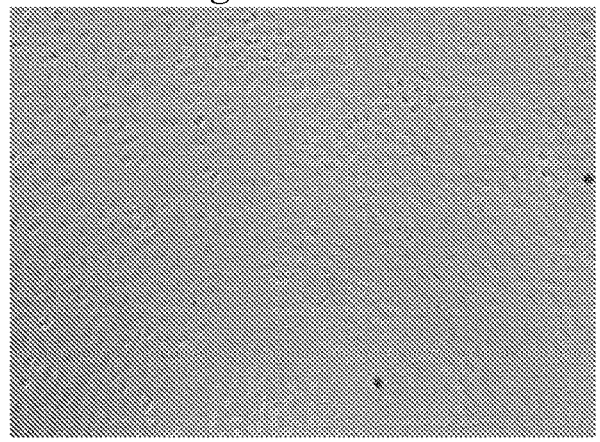
Figure 8E:
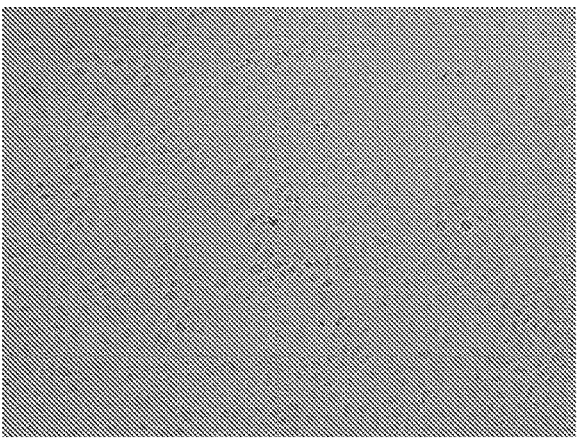
Figure 8H:
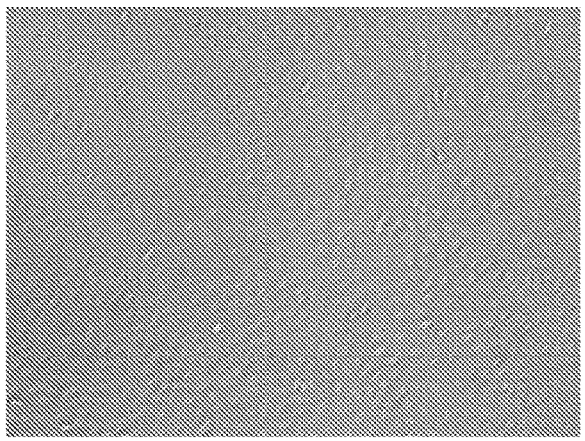
Figure 8F:
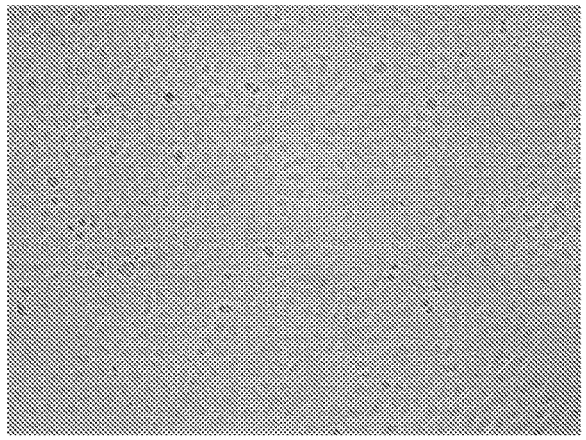
Figure 8I:
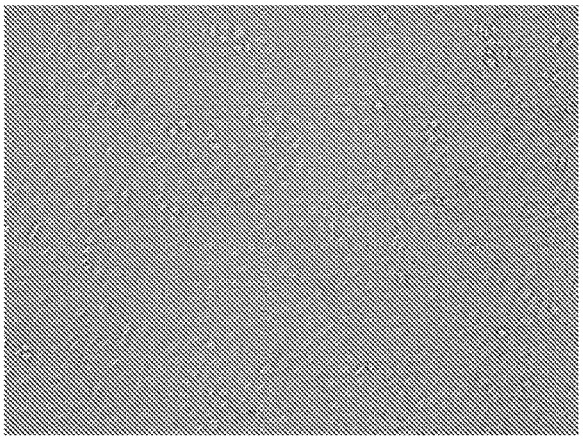
Figure 8G:
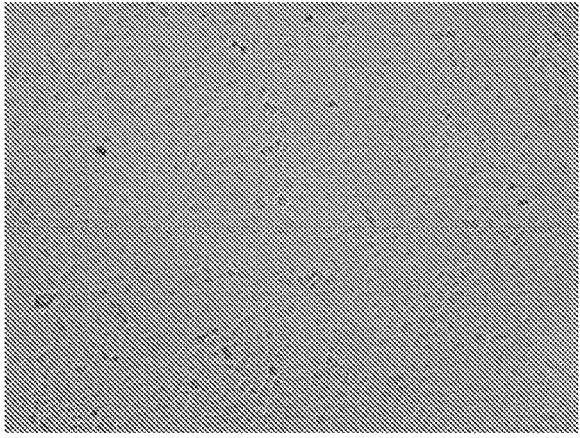
Figure 8J:
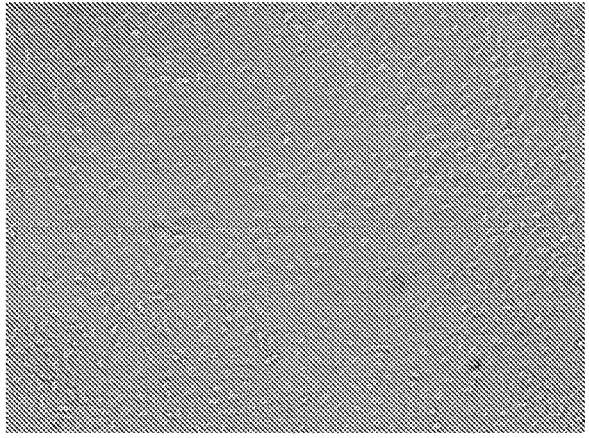
Figure 8K:
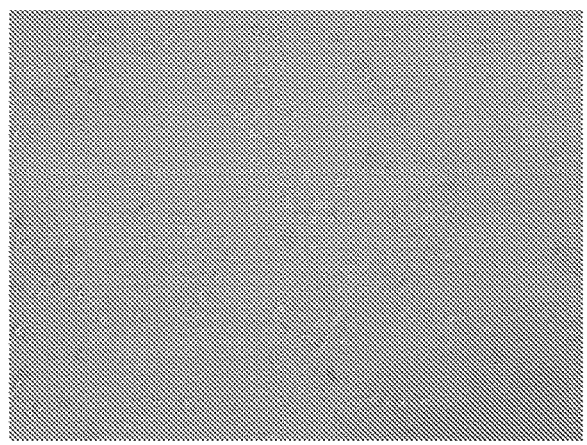
Figure 8L:
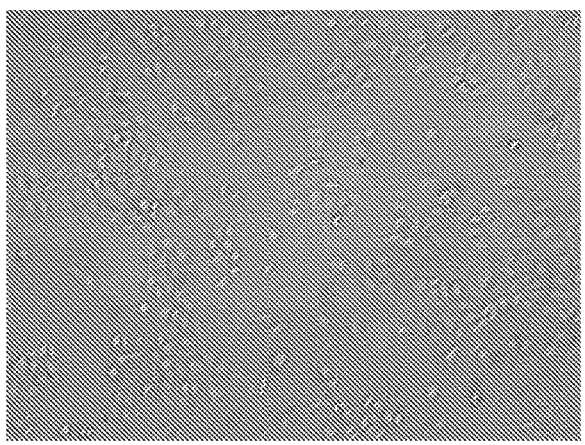
Figure 8M:
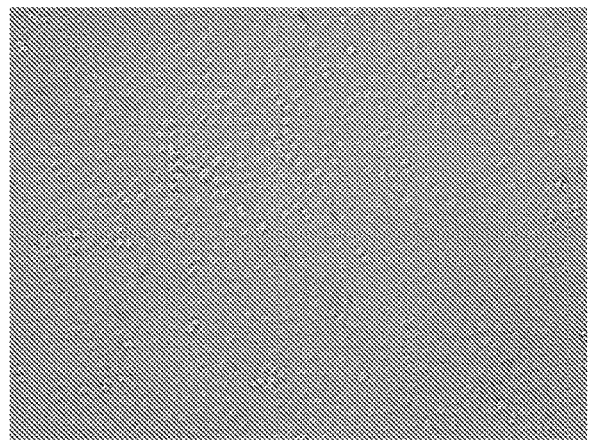
Figure 9A:
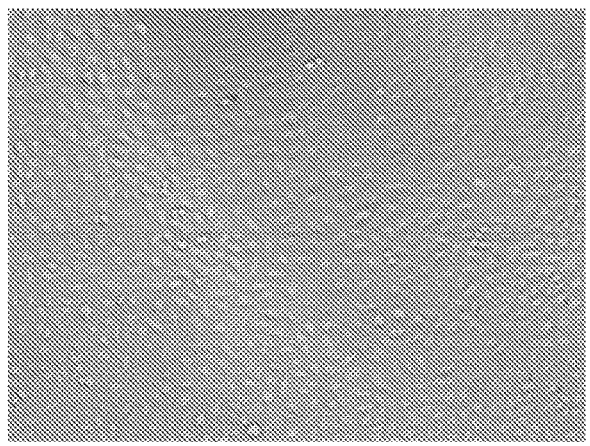
FIG. 9A (T=0) and 9B (T=48 h) are used as a control.
Figure 9B:
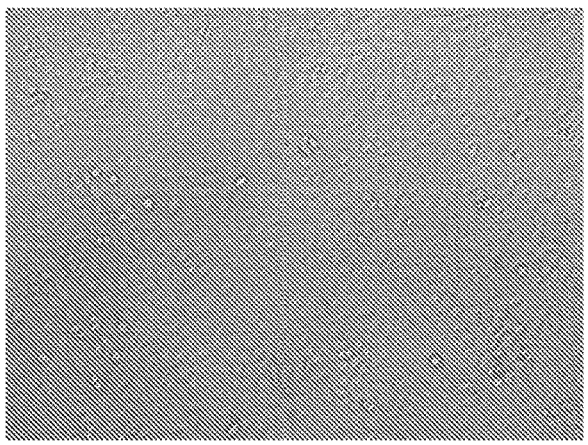
FIG. 9B-9E were taken 48 hours after the treatment.
Figure 9D:
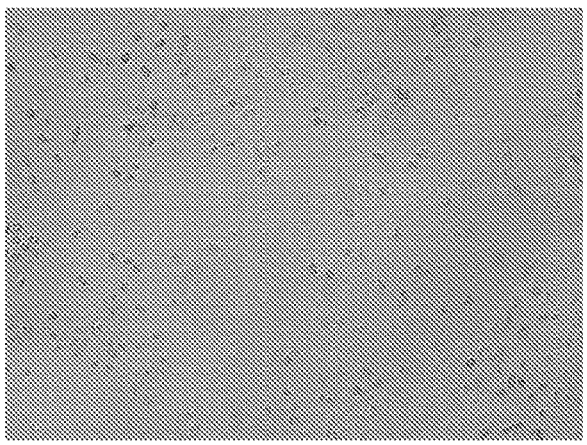
Figure 9C:
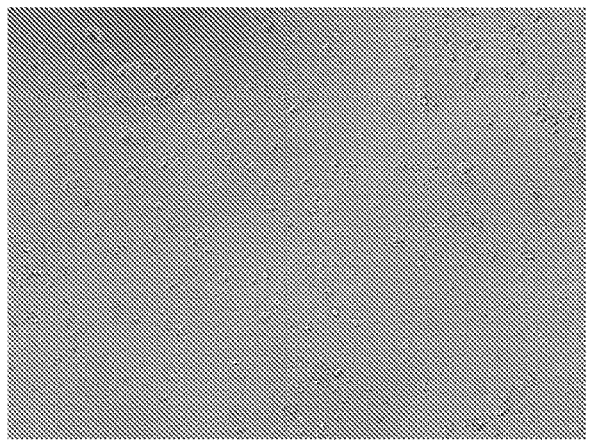
Figure 9E:
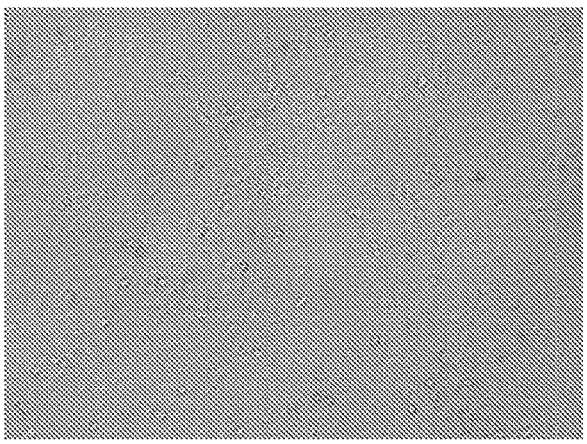
Figure 10:
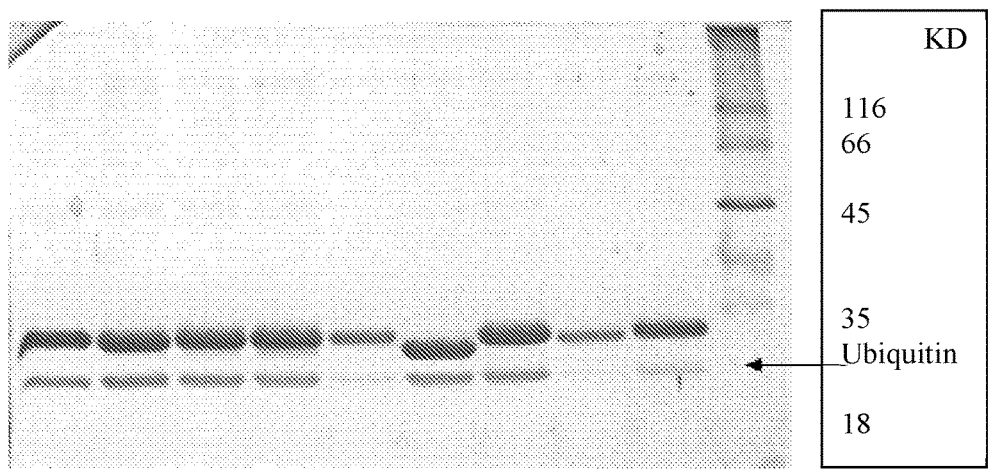
FIG. 10 shows the Coomassie Plus stained electrophoresis gel of selected peptides: lanes (from left to right): 1—E7.1; 2—E10.2; 3—E13.3; 4—E14.1.1; 5—E14.1.4; 6—E23I3; 7—E23I5; 8—E15.1.3-T; 9—A4.3.12-T; 10—Protein Marker (Fermentas).

It can be seen from the results (see FIG. 3), most of the peptides gave higher fluorescence than the positive control (that contained no peptide; orange dot), and more than the non eEF2-binding control peptide at concentration of 5 μM. That means that they enhanced protein synthesis, when TB2 and GW provided the highest effect.

Example 5. Preparation of Multi-Armed PEG Complex Loaded with 2 Targeting Peptides and 2 Toxins A construct of a branched PEG molecule covalently coupled with two different cancer-targeting moieties and two different toxin moieties was designed and synthesized (the schematic representation of the scaffold is shown in FIG. 1). The targeting moieties included in this example construct were the cyclic peptides E13.3 (consisting of SEQ ID NO:1) and PD-L1-GR (consisting of SEQ ID NO:2), and the toxin moieties were the cyclic peptides Tox1 (consisting of SEQ ID NO:3), and Tox2 (consisting of SEQ ID NO:4).

The preparation method comprised two steps. At the first step a branched PEG containing eight arms was produced in which seven arms were coupled with targeting/toxin moieties (protected peptides) and one with a Lysine residue protected with FMOC (Fmoc-Lys). At the second step eight of the peptide/toxin-PEG molecules produced in step 1 were coupled to another branched PEG molecule of eight arms to obtain a construct of multi-branched PEG coupled with 56 toxin/targeting moieties, of which 42 moieties are toxin peptides (21 Tox1 and 21 Tox2), and 14 are targeting peptides (7 copies of EGRF targeting peptide E13.3 and 7 copies of PD-L1 targeting peptide PD-L1-GR).

In more details:

Step 1—Preparation of Branched PEG Coupled with One Type of Targeting or Toxin Moiety 2.4 μmole of a targeting peptide or 7.3 μmole of toxin peptide were dissolved in DMSO.

All peptides have only one primary amine, except for E13.3, which has 3, of which one is protected with dde, and the N-terminal is blocked with acetate residue.

5.9 mg Fmoc-Lys-OH (Novabiochem (Merck) Cat. Num. 852023; MW=368.43) was dissolved in 150 μl of HCl 0.1 M, followed by addition of 650 μl of DMSO to reach a concentration of 20 mM.

33.4 mg of 8-arm star PEG-NHS (Mw 10 KDa, Creative Biotechnologies) were dissolved in 167 μl of dioxane to reach a concentration of 20 mM.

Each of the targeting peptides solutions were mixed with 17 μl of Fmoc-Lys-OH solution and 17 μl of PEG solution.

Each of the toxin peptides solutions were mixed with 52 μl of Fmoc-Lys-OH solution and 52 μl of PEG solution. Each mix was supplemented with TEA (trimethylamine) to 5%. Each solution was incubated for 15.5 hours at room temperature on a Rotamix at 30 rpm to obtain a clear solution of 8 armed PEG coupled with 7 molecules of a specific targeting/toxin moiety and one arm containing a primary amine (The Fmoc protection is removed in this process to give one free primary amine on each PEG molecule).

The branched PEG-peptide molecules are denoted PEG-E13.3, PEG-PD-L1-GR, PEG-Tox 1 and PEG-Tox 2.

Step 2—Construction of Multi-Branched PEG Construct Coupled to 56 Targeting/Toxin Moieties.

The branched PEG-peptide solutions: PEG-E13.3, PEG-PD-L1-GR, PEG-Tox1 and PEG-Tox2 were mixed together with 20 mM PEG-NHS solution in a stoichiometric molar ratio of PEG-NHS:PEG-E13.3:PEG-PD-L1-GR:PEG-Tox1:PEG-Tox2 of 1:1:1:3:3, and incubated for 2 hours at room temperature on a Rotamix at 30 rpm, followed by slow addition of 80% hydrazine to a final concentration of 5%. Hydrazine was used to remove the dde protecting group from the E13.3 moiety. The mixture was incubated for 2 hours at room temperature on a Rotamix at 30 rpm. The resultant construct is a multi-branched PEG coupled with 56 targeting/toxin moieties: 7 copies of E13.3 peptide, 7 copies of PD-L1-GR peptide, 21 copies of Tox1 and 21 copies of Tox 2. At the end of the reaction, PBS was added with gentle mixing.

Step 3—Ultrafiltration

The samples were ultrafiltrated with two additions of 20 ml PBS using Vivaspin 20 concentrator (30 K MWCO PES) to a concentration of ~206 μM of loaded multi-armed PEG denoted as PEG-E13.3-(PD-L1-GR)-Tox1-Tox2, and the buffer was substituted to PBS.

In a similar way, additional multi-branched PEGs carrying alternative toxins or peptides (such as BIM) were produces. Examples of such multi-armed PEG is PEG-E13.3-PD-L1-GR-BIM, in which the toxins Tox 1 and Tox 2 were substituted by BIM.

Example 6. Toxicity of a Construct Comprising E13.3, Tox1 and Tox2

A construct comprising a multi-arm-PEG scaffold bound to E13.3 targeting peptide having the sequence SEQ ID NO: 1 (CHPGDKQEDPNCLQADK) and a toxin selected from BIMBH3 (referred also as BIM and having the sequence SEQ ID NO: 5 MRPEIWIAQELRRIGDEFNA) or a combination of Tox1 and Tox2 was generated. The scaffolds were prepared as described in Example 5 and is denoted as PEG-E13.3-Tox1-Tox2 and PEG-13.3-BIM, accordingly Cells Culture and Seeding:

A431 cells (human squamous carcinoma express about 100,000 copies of EGFR on each cell) and MCF-7 cells (breast cancer cell expressing about 3,000 copies of EGFR on each cell) were thawed and cultivated to achieve exponentially growing cultures. Cells were collected, counted and seeded at the density of 7,000 cells/well and 5,000 cells/well, respectively, in a 96 well tissue culture plate.

The plates were incubated until the next day at the following conditions: 37±1° C., humidified, and 5±0.5% $CO_2$/air, to enable cells adherence to the wells.

Treatment:

The cell viability of A549 cell was tested using Alamar Blue viability assay. At the next day following the seeding, Growth Media was replaced with 200 μl Assay Media that contained 2% FBS and Test Items at different concentrations of the construct (1, 3 and 8 μM), or Vehicle Control (PBS; concentration-0). Plates were incubated at 37±1° C., humidified 5±0.5% $CO_2$/air. After 48 hours of incubation, images of cells treatments were taken on microscope (see FIGS. 4-7).

Several concussions can be made from these experiments. First, it can be seen on the figures that the typical cells aggregates characterizing A431 and MCF-7 disappeared when a construct comprising PEG-E13.3 and any one of the toxin was added (FIGS. 5-6). Moreover the phenomena was dose dependent. However, when the construct lacked E13.3 peptide (FIG. 7), increasing the concentration of the toxin did not increase the ratio of dead cells significantly and actually was not different from the control. This result clearly indicate that E13.3 targeted the construct to the cell.

Second, the proportion of dead cells increased with increasing the concentration of the toxins (for both, BIM and combination of Tox1 and Tox2), indicating for dose dependent effect. Moreover, comparing the images obtained for BIM and a combination of Tox1 and Tox2, it can be seen that the combination was more potent causing to more severe cell death. As expected MCF-7 cells, expressing less EGFR were less sensitive than A431 cells.

Concluding all said above it is clear that a construct comprising a toxin such as Tox1, Tox2 or a combination thereof and targeting peptides, wherein at least one of them is E13.3 are potent in targeting and treating cancer.

Example 7. Cytotoxicity of the Constructs as Tested on A431 Cells

In condition similar to those of Examples 5 and 6, PEG-PD-L1-GR-BIM, PEG-E13.3-BIM and PEG-E13.3-PD-L1-GR-BIM constructs were prepared and tested for cytotoxicity using A431 cells and Alamar Blue Blue viability assay varying the concentration of the construct from 10 nM to 1 μM. After 48 hours of incubation, images of cells treatments were taken on microscope.

The results are presented in FIG. 8. It can be seen that the construct PEG-PD-L1-GR-BIM and PEG-E13.3-BIM had limited ability of killing A431 cells at 1 μM concentration. The combination of E13.3 and PD-L1-GR targeting peptides on the other hand provided killing or more than 60% of the cells. Actually the cytotoxic effect of the construct comprising both targeting peptides was higher than the additive effect of the two constructs comprising one of two these peptides. This clearly indicates for the synergistic cytotoxic effect that the construct comprising two targeting peptides and a combination of Tox1 and Tox2 has.

Example 8. Effect of PEG-E13.3-(PD-L1-GR)-Tox1-Tox2, and PEG-E13.3-(PD-L1-GR)-BIM Constructs on the Growth and Viability of A549 Cell Line Materials and Methods The test items PEG-E13.3-(PD-L1-GR)-Tox1-Tox2, and PEG-E13.3-(PD-L1-GR)-BIM were prepared as described in Example 5 and were used at concentration of 10 μM. Phosphate Buffered Saline (PBS) is used as a control.

A-549 cells (human lung tumor cells) were thawed and cultivated to achieve exponentially growing cultures. Cells were collected, counted and seeded in a 96 well tissue culture plate at the following densities: A-549: 5,000 cells/well.

The plate was incubated until the next day at 37±1° C., humidified, 5±0.5% $CO_2$/air, to enable cells adherence to the wells.

Treatment

At the next day after the seeding, Growth Media were replaced with Test Items Solutions prepared in Assay Medium (2% f FBS). Test Items Solutions are applied carefully (onto the sides of the well, not directly onto the cells) in volume of 200 μl/well to achieve the final concentrations as following: PEG-E13.3-(PD-L1-GR)-Tox1-Tox2: 3 or 10 μM and PEG-E13.3-(PD-L1-GR)-BIM—10 μM.

The plate was incubated at 37±1° C., humidified 5±0.5% $CO_2$/air.

After 48 hours of incubation, representative images of cells treatments were taken on microscope. The results are presented on FIG. 9

Results

As can be clearly seen from FIG. 9 PEG-E13.3-(PD-L1-GR)-Tox1-Tox2 was effective in killing A549 cell both in concentration of 3 and 10 μM. Interestingly, PEG-E13.3-(PD-L1-GR)-Tox1-Tox2 at the concentration of 3 μM it was much more efficient than 10 μM PEG-E13.3-(PD-L1-GR)-BIM construct comprising well known BIM toxin.

Example 9. Acute IV Toxicity of PEG-E13.3-(PD-L1-GR)-Tox1-Tox2 in Mice

PEG-E13.3-(PD-L1-GR)-Tox1-Tox2 was prepared as described in Example 5 and injected intravenously to 3 Female Hsd:ICR (CD-1®) mice, 7 weeks old using 4 ml/kg dose according to the regiments described in Table 3.

TABLE 3

Administration schedule

| Group & Sex | Animal No | Dosing session | Dosing on Study day | Concentration (μM) | Volume | Observation period following administration |
|---|---|---|---|---|---|---|
| 1F | 1, 2, 3 | 1 | 0 | 25 | 4 | 5 |
|  |  | 2 | 6 | 75 |  | 14 |

The weight and individual clinical signs were observed for 20 days. No significant abnormalities were seen neither in weight nor in the tested clinical signs. The animals were euthanized on day 20 and individual gross necropsy was performed. No abnormality was detected during the examination. Results of this example clearly indicate that PEG-E13.3-(PD-L1-GR)-Tox1-Tox2 construct is perfectly safe in vivo.

Example 10. Evaluation of Antitumor Effect of PEG-E13.3-(PD-L1-GR)-Tox1-Tox2 In Vivo Material and Methods Animals: 18 athymic nude female mice 6-7 weeks old divided into 3 groups (1 control group and 2 test items groups) are allowed to accumulate for at least 5 days. Following acumulation, A431 tumor cells are subcutaneously injected to right flan region of each mouse, the day of injection is denoted as Day 0.

The following parameters are monitored: weight (twice a week), tumor size (measured with digital caliper and the tumor volume is calculated as width$^2$×length/2.

When the tumor reaches the size of 100-150 mm3, mice are subbbjected to 3 IV injections of test items during the first week. Animals are observed from additional 3 weeks.

Following observation period, mice are euthanized, the tumor is excised, measured and fixed in 4% formaldehyde solution for further analysis.

Example 11: Antagonist of EGF Receptor: Screening, Purification

Screening

Using the technique described in WO 2007/010525, a series of new peptides (cyclopeptides) binding to human Epidermal Growth Factor Receptor (EGFR) were generated and tested. After identification of several potential peptide, a few further cycles of optimization were performed. One of the peptides, denoted as E13.3 and having the sequence of CHPGDKQEDPNCLQADK (SEQ ID NO: 1) showed high affinity to the receptor at its binding site.

Expression and Purification

Bacteria comprising plasmids for expression of the identified peptides E7.1, E10.2, E10.3, E13.3, E15.1.3-T, E14.1.1, E14.1.4, E23I3, E23I5 and A4.3.12-T were started with 2.5 μl of cells comprising the plasmid of a relevant peptide in 5 ml 2YT medium with ampicillin and grown at 38° C. over night at 350 rpm. 2 ml of each starter were grown in 50 ml 2YT at 37° C.; the expression was induces with IPTG, 0.43 mM at OD 1.5-2.5 for 3 hours following which the cells were centrifuged and kept at −20° C.

The cells were lysed with lysozyme in the presence of DNases I and B-Per (Bacterial Protein Extraction Reagent), and the peptides were purified by affinity chromatography using Ni-NTA beads in a batch mode. Shortly, the peptides were loaded on Ni-NTA beads in the presence of 20 mM Imidazole, washed with PBS and eluted with 250 mM Imidazole. The buffer was exchange using PALL Life Sceince, Nanosep Centrifugal devices, 3K gray. The quantity of the peptides was tested by Coomassie Plus Protein Assay (see FIG. 10).

Example 12. The Effect of the Peptides on EGFR

The effect of several peptides on the phosphorylation levels of human EGFR in human epidermoid carcinoma cell line A431 was assessed by ELISA test. Briefly, exponentially growing A431 cell culture were detaches from the flask with 0.25% trypsin/EDTA solution, and 200 μl of cell suspension were transferred to 96-well plates at the concentration of 2×10$^5$ cells/ml and grown for about 3 days. Following medium exchange, 50 μl EGF dilutions and EGF+peptides (50 ng/ml and 0.2 mg/ml, respectively) were added. The plate was incubated for 7.5 min at 37° C. EGF-containing medium was removed and the cells were fixed by 150 ul of fixing solution and incubated for 20 min. at room temperature, following which the plate was washed 2 times with triton washing solution. The level of phosphorylates was assessed by incubation with phospho-EGFR (Tyr1045) antibody as a primary antibody and Anti-rabbit IgG as a secondary antibody. The ability of different peptides to inhibit auto-phosphorylation of EGFR is presented on FIG. 2. The normalized percent of inhibition (of the EGFR auto-phosphorylation is presented in FIG. 11 and Table 4. The normalized percent of inhibition is calculated as the fluorescence signal of the test item divided by the fluorescence signal of the control that contains no test item, with the same concentration of EGF.

TABLE 4

| Normalized Percent of EGFR autophosphorylation inhibition | | | | | | | | | |
|---|---|---|---|---|---|---|---|---|---|
| | Clone | | | | | | | | |
| | A4.3.12 | E23I5 | E23I3 | E14.1.4 | E14.1.1 | E15.1.3 | E13.3 | E10.2 | E7.1 |
| % Inhibition | 23 | 35 | 66 | 72 | 80 | 61 | 99.4 | 68 | 30 |

Figure 11:
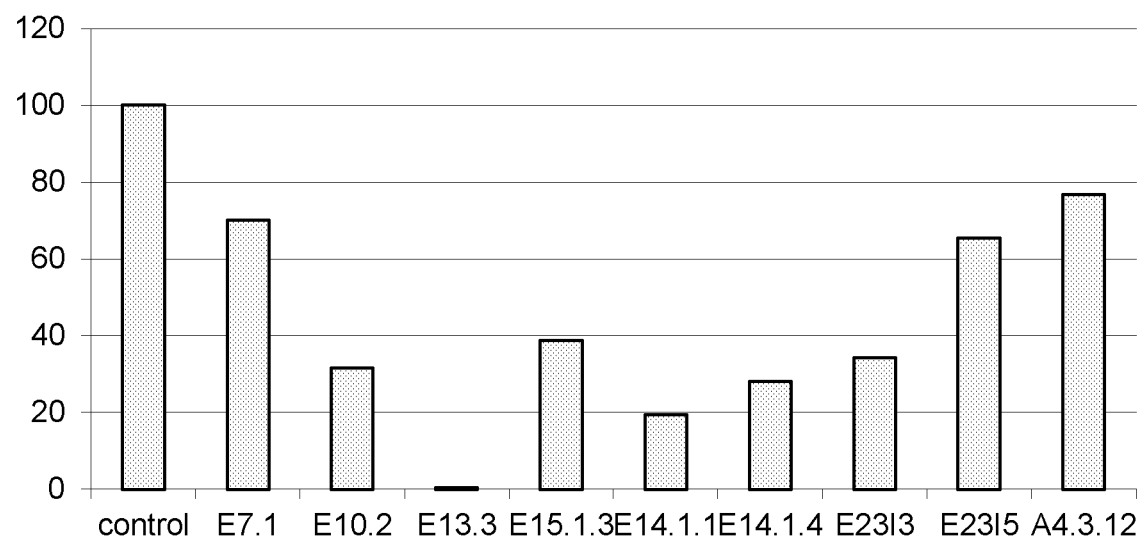
FIG. 11 shows the normalized results of inhibition analysis of the selected peptides by measuring auto phosphorylation of EGFR.

As it can be clearly seen from the FIG. 11 and Table 4, E13.3 has the higher inhibitory activity among the peptides, having calculated $IC_{50}$ of 2 µM.

Example 13. Stability of E13.3 in Bovine Serum

Figure 12:
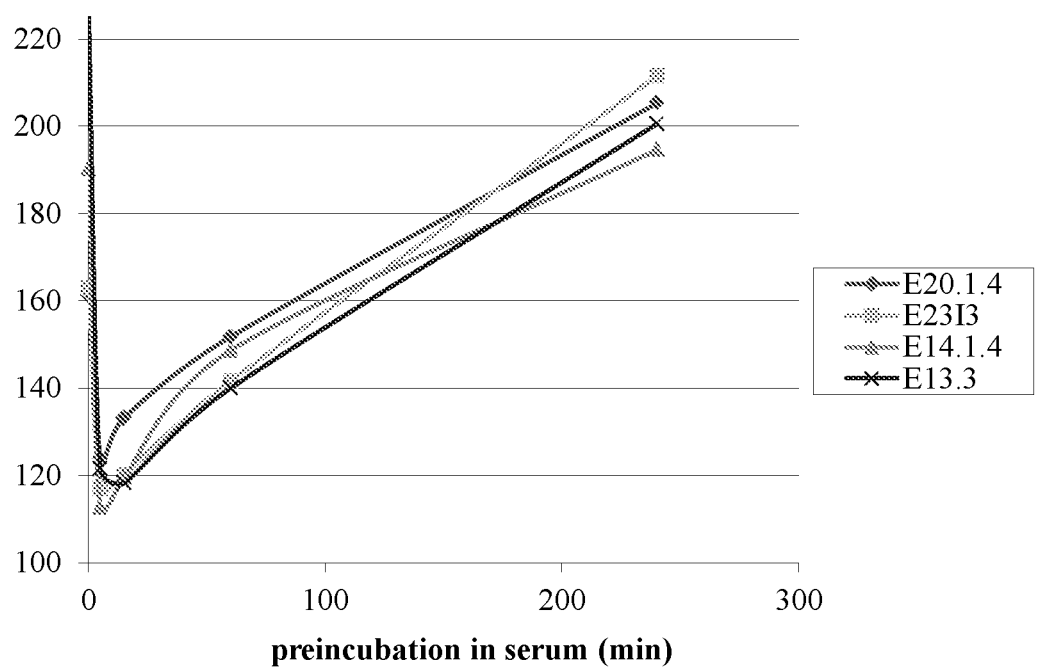
FIG. 12 shows the result for measurement of the stability of selected peptides incubated in bovine serum for different time periods.

The stability of the selected peptides in bovine serum was assessed by measurement of the inhibitory activity of the peptides after incubation of the peptides with bovine serum. The inhibitory activity was measured as described in Example 12. The inhibitory activity of the peptide was assessed following incubation of the peptides with bovine serum at 37° C. for different periods of time. EGF concentration in the samples was 50 ng/ml. The results are presented in FIG. 12. It can be clearly seen that all peptides have similar stability in the bovine serum with $t_{0.5}$ of about 1.5 hours.

Example 14. Inhibition Efficacy of the Peptides is Dose Dependent

Figure 13A:
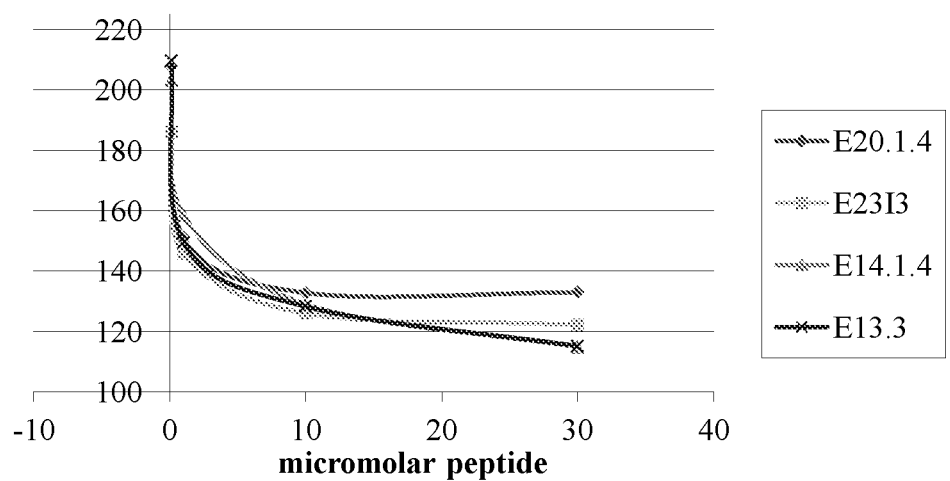
FIG. 13 shows the result of assessment of inhibitory activity of the selected peptides at different concentrations (FIG. 13A general view and FIG. 13B shows E13.3 alone).
Figure 13B:
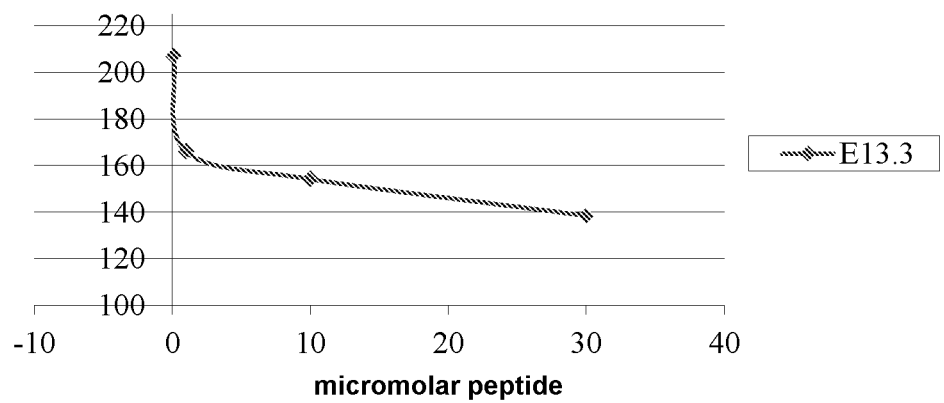

Efficacy of different concentration of the selected peptide was assessed by ELISA in a similar was as in Example 12. The results are presented in FIG. 13. The $IC_{50}$ of all peptides was about 0.5-1 µM.

Example 15. Preparation of E13.3 Bound to 8-Arm PEG 9.8 mg of E13.3(fmoc) Lys was dissolved in water to the final concentration of 20 mg/ml. 11.3 mg of 8 arm PEG Succinimidyl Carboxymethyl Ester, MW 73,000 (JENKEM TECHNOLOGY USA INC) with 565 µl dioxane was heated at 37° C. to a complete dissolution. E13.3 and PEG solution were mixed in the presence of 50 µl TEA and incubated overnight at room temperature. To the obtained solution, 50 µl piperidine was added and incubated for 0.5 at room temperature. To the solution, 1 ml of ethyl acetate was added to obtain a suspension which was than centrifuged and the upper phase was removed. These steps of washing with ethyl acetate were repeated 4-5 times. Finally, the upper phase was removed completely and the remained pellet was dissolved in 200 µl PBS. The buffer was further exchanged to PBS using Vivaspin 20 ml Concentrator to eliminate any traces of ethyl acetate.

Example 16. Stability of E13.3 in Mice

Figure 14:
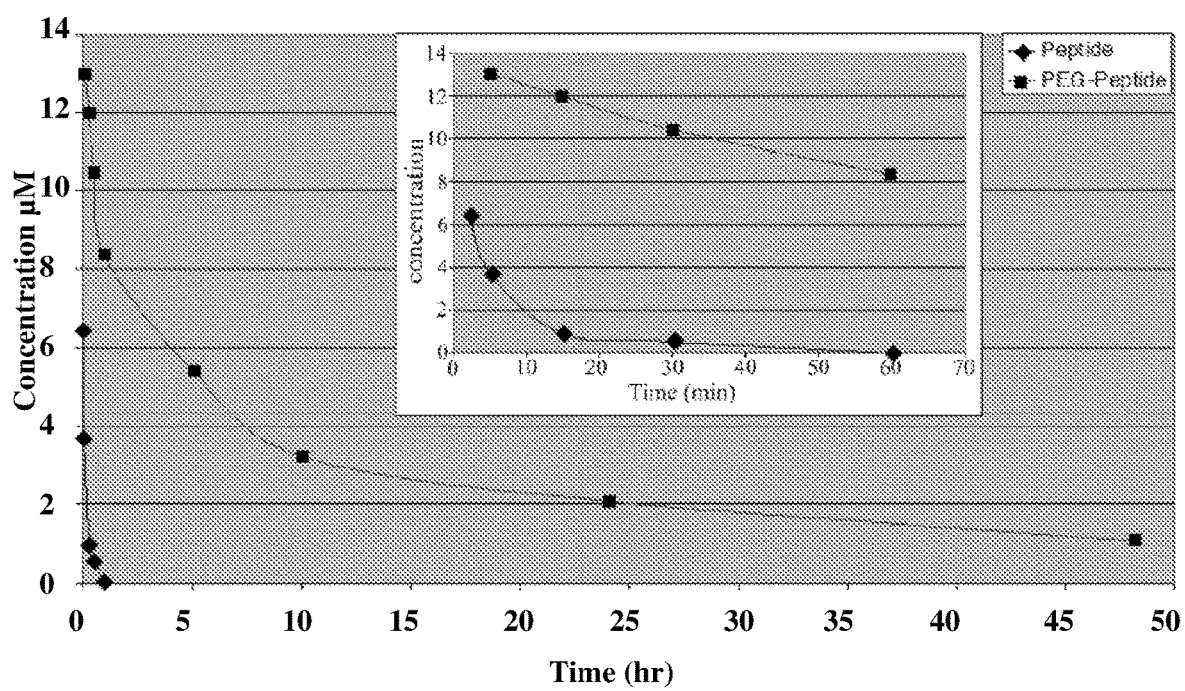
FIG. 14 shows the in vivo stability of E13.3 peptide alone or in complex with 8-armed PEG.

The stability of the fluorescently marked peptide E13.3 alone or bound to 8-armed PEG was evaluated in vivo by injecting the compounds to the tail vein of mice. The blood of the animals was analyzed for the presence of the peptide (fluorescence) at different time intervals. It can be clearly seen from the result presented in FIG. 14 that $t_{0.5}$ of the free peptide is much shorter (about several minutes) than that of the peptides bound to PEG ($t_{0.5}$ of about 3.5 hours).

Figure 15:
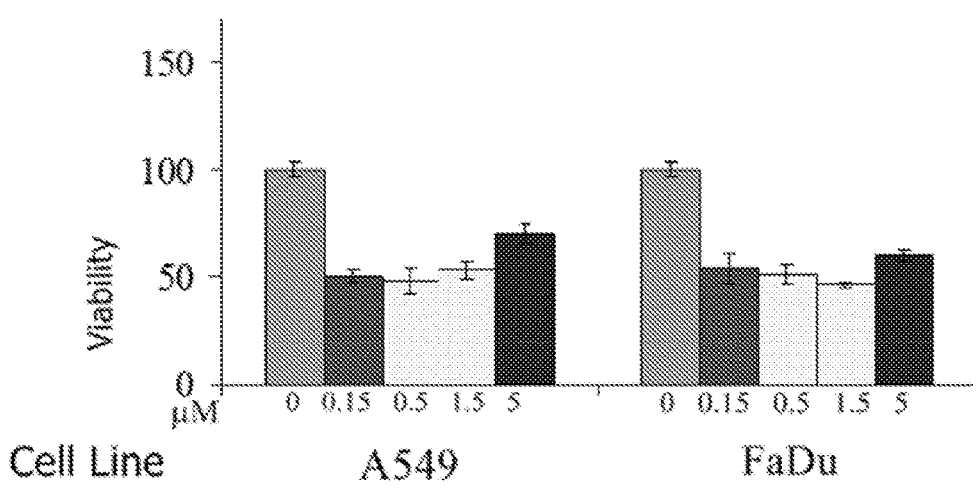
FIG. 15 shows the effect of E13.3 on viability of two cancer cell lines.

Example 17. The Effect of E13.3 on the Viability of Different Cancer Cell Lines The anti-cancer activity of E13.3 was assessed using several cancer cell lines (A549—human lung carcinoma cell line and FaDu—human pharyngeal carcinoma cell line). The cell cultures were incubated in the presence or absence of E13.3 (at different concentrations) and tested for viability using alamarBlue reagent. The results are presented on FIG. 15. It can be seen, that E13.3 bound to PEG could successfully reduce the viability of the cancer cells in all tested concentrations.

Example 18. Accumulation of Fluorescent PEG-E13.3 in Cancer Tumors

E13.3-PEG was labeled with Flourescein and injected IV to Xenograft mice bearing subcutaneous NCI-H1650 tumor (lung cancer). Following anesthesia, kidney, liver and tumor were collected at specific time points and the fluorescence was measured. The results are presented in FIGS. 16 and 17.

Figure 16:
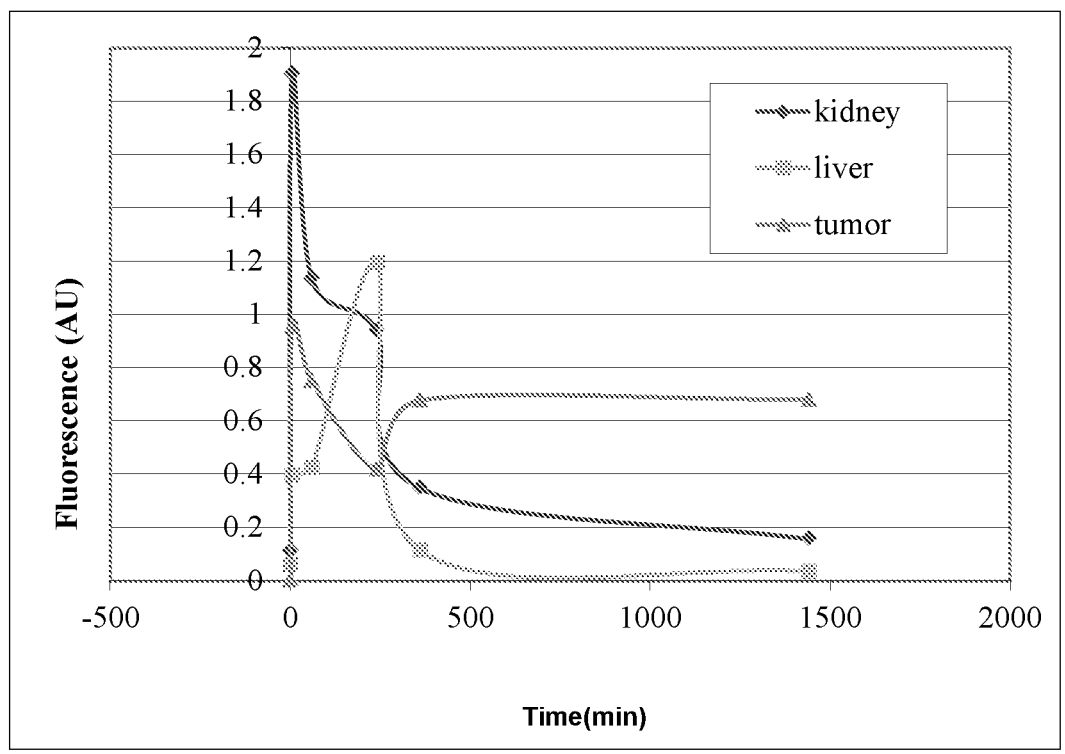
FIG. 16. shows the accumulation of E13.3-PEG complex in kidney, liver and tumor in mice.
Figure 17:
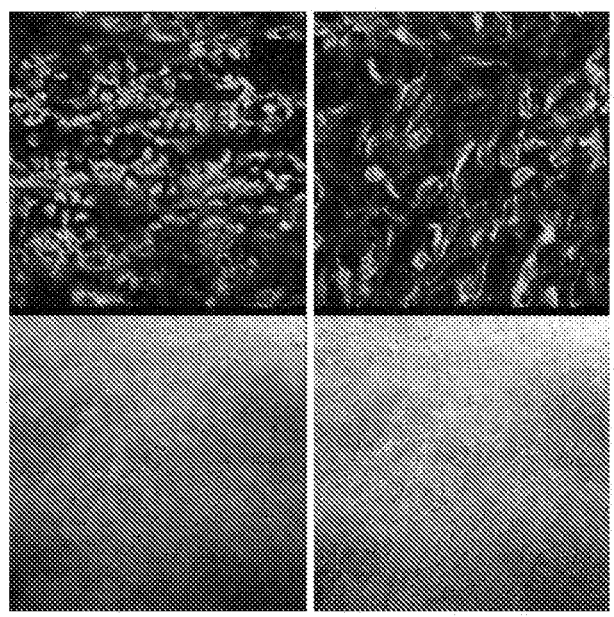
FIG. 17 show a picture of cancer cells that were isolated from a tumor in mice 1 hour (left panel) and 24 hour (right panel) following IV injection of fluorescently marked E13.3-PEG complex.
Figure 18A:
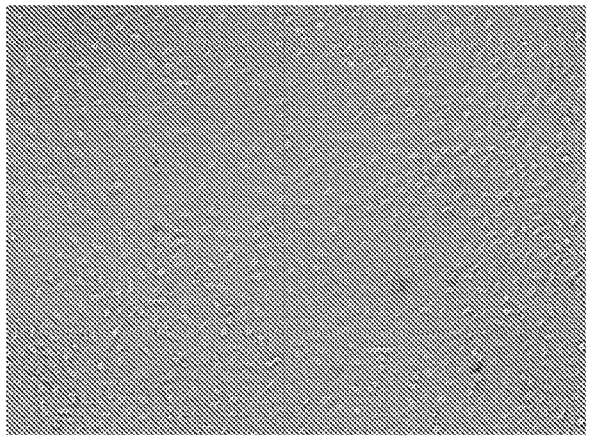
FIG. 18 shows the effect of the treatment of A-549 cells with 1 µM of: PEG-E13.3-BIM (18B), PEG-(PD-L1-GR)-BIM (18C) and PEG-E13.3-(PD-L1-GR)-BIM (18D) using PBS as a control (18A).
Figure 18B:
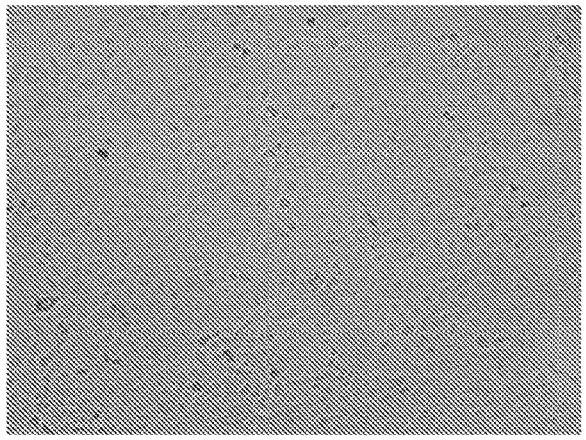
Figure 18C:
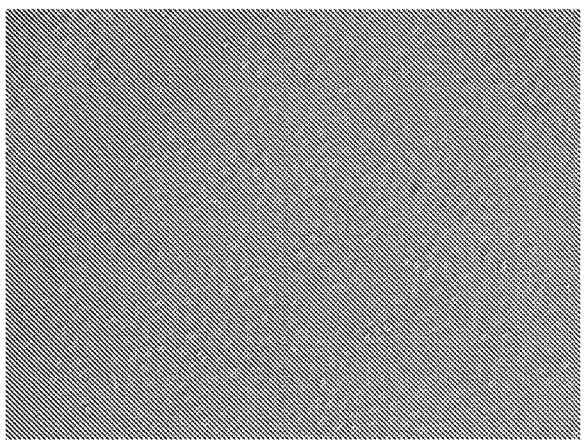
Figure 18D:
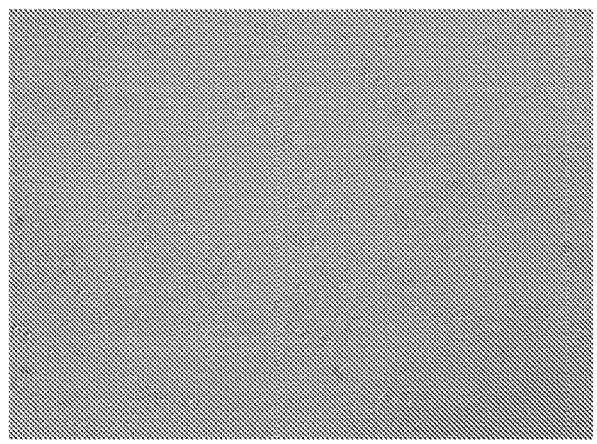

As it can be seen from FIG. 16, there was a fast increase in the fluorescence in kidney and liver with a typical elimination curve afterwards. Contrary to that, the fluorescence was accumulated in the cancer cells indicating that E13.3 effectively binds, enters and accumulated in the cancer cells. Results shown on FIG. 17 further support that most of the cancer cells interact with E13.3-PEG and internalize the fluorescent peptide.

Example 19: PD-L1 Binding Proteins

Screening

Using the technique described in WO 2007/010525, a series of new peptides (cyclopeptides) binding to binding to a human PD-L1 were generated and tested. After identification of several potential peptides, a few further cycles of optimization were performed. One of the peptides, denoted as PD-L1-GR and having the sequence of CysGluGlyLeu-ProAlaAspTrpAlaAlaAlaCys (SEQ ID NO: 2) showed high affinity to the receptor at its binding site.

Example 20. Preparation of PD-L1-GR Peptide Bound to Multi-Armed PEG Construct Multi-armed PEG constructs comprising (i) PD-L1-GR cyclic peptide and BIM-BH3 (denoted as PEG-(PD-L1-GR)-BIM), (ii) E13.3 targeting peptide (SEQ ID NO:1) and BIM-BH3 toxin (denoted as PEG-E13.3-BIM), and (iii) E13.3, PD-L1-GR and BIM-BH3 toxin (denoted as PEG-E13.3-(PD-L1-GR)-BIM) were prepared as described in Example 5.

The constructs were used as Test Items in cell proliferation assay in concentration of 1 µM. PBS was used as a control. For the assay, A549 cells (human lung carcinoma cell line) were thawed and cultivate to achieve exponentially growing. The cells were collected, counted and seeded at the density of 7,000 cells/well in a 96 well tissue culture plate. The plate was incubated until the next day at 37±1° C., humidified, 5±0.5% $CO_2$/air, to enable cells adherence to the wells. At the next day, Growth Media are replaced with Test Items Solutions prepared in Assay Medium (2% fFBS). Test Items Solutions are applied carefully in volume of 200 µl/well to achieve the final concentrations of the Test Items of 1 µM. After 48 hours of incubation, representative images of cells treatments were taken on microscope and are presented in FIG. 18.

It can be seen from FIG. 18, the construct comprising PEG-E13.3-(PD-L1-GR)-BIM was the only construct to inhibit cell proliferation at a concentration of 1 µM. This indicates that the complex comprising a combination of E13.3 and PD-L1-GR peptides has significantly higher cytotoxicity than the combined cytotoxicity of the constructs comprising only one of the peptides.

Although the present invention has been described herein above by way of preferred embodiments thereof, it can be modified, without departing from the spirit and nature of the subject invention as defined in the appended claims.

The invention claimed is:

1. A pharmaceutical composition comprising:
   A. a construct comprising:
      (i) multiple copies of at least two different peptides that bind specifically to at least two different extracellular tumor antigens, respectively; and
      (ii) multiple copies of at least two peptide toxins,
   wherein the peptides and the peptide toxins are covalently bound to an organic scaffold carrier,
      wherein each one of the peptides and peptide toxins consists of up to 50 amino acids,
      wherein the organic scaffold comprises a polyethylene glycol (PEG) molecule or a modified PEG molecule,
      wherein the organic scaffold comprises a plurality of sites available to bind the peptides and the toxins,
      wherein the at least two different peptides include a peptide having the amino acid sequence of SEQ ID NO: 1, and a peptide having the amino acid sequence of SEQ ID NO: 2, and
      wherein the at least two peptide toxins include a peptide toxin having the amino acid sequence of SEQ ID NO: 3 and a peptide toxin having the amino acid sequence of SEQ ID NO: 4, and
   B. a pharmaceutically acceptable excipient.

2. A method of treating cancer in a subject in need thereof comprising administering to said subject the pharmaceutical composition according to claim 1.

3. An isolated polynucleotide comprising a sequence encoding a polypeptide comprising (i) at least one copy of SEQ ID NO: 1; (ii) at least one copy of SEQ ID NO: 2; (iii) at least one copy of a sequence selected from SEQ ID NO: 3, SEQ ID NO: 4 and combinations thereof.

4. A construct comprising
   (i) multiple copies of at least two different peptides that bind to at least two different extracellular tumor antigens, respectively, and
   (ii) multiple copies of at least two peptide toxins,
   wherein the peptides and the toxins are covalently bound to an organic scaffold carrier,
   wherein each one of the peptides and peptide toxins consists of up to 50 amino acids,
   wherein the organic scaffold comprises a polyethylene glycol (PEG) molecule or a modified PEG molecule,
   wherein the organic scaffold comprises a plurality of sites available to bind the peptides and the toxins,
   wherein the at least two different peptides include a peptide having the amino acid of SEQ ID NO: 1 and a peptide having the amino acid of SEQ ID NO: 2, and
   wherein the at least two peptide toxins include a peptide toxin having the amino acid sequence of SEQ ID NO: 3 and a peptide toxin having the amino acid sequence of SEQ ID NO: 4.

* * * * *

SEQUENCE LISTING

<160> NUMBER OF SEQ ID NOS: 5

<210> SEQ ID NO 1
<211> LENGTH: 17
<212> TYPE: PRT
<213> ORGANISM: Artificial Sequence
<220> FEATURE:
<223> OTHER INFORMATION: peptide

<400> SEQUENCE: 1

Cys His Pro Gly Asp Lys Gln Glu Asp Pro Asn Cys Leu Gln Ala Asp
1               5                   10                  15

Lys

<210> SEQ ID NO 2
<211> LENGTH: 12
<212> TYPE: PRT
<213> ORGANISM: Artificial Sequence
<220> FEATURE:
<223> OTHER INFORMATION: peptide

<400> SEQUENCE: 2

Cys Glu Gly Leu Pro Ala Asp Trp Ala Ala Ala Cys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: peptide

<400> SEQUENCE: 3

Cys Ser Ala Arg Trp Gly Pro Thr Met Pro Trp Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: peptide

<400> SEQUENCE: 4

Cys Arg Arg Gly Ser Arg Ala Ser Gly Ala His Cys
1               5                   10

<210> SEQ ID NO 5
<211> LENGTH: 20
<212> TYPE: PRT
<213> ORGANISM: Artificial Sequence
<220> FEATURE:
<223> OTHER INFORMATION: peptide

<400> SEQUENCE: 5

Met Arg Pro Glu Ile Trp Ile Ala Gln Glu Leu Arg Arg Ile Gly Asp
1               5                   10                  15

Glu Phe Asn Ala
            20